(12) United States Patent
Zhao et al.

(10) Patent No.: US 11,969,719 B2
(45) Date of Patent: Apr. 30, 2024

(54) POLYDENTATE ORGANIC LIGAND, PREPARATION METHOD AND APPLICATION THEREOF, METALLO-SUPRAMOLECULAR POLYMER AND PREPARATION METHOD THEREOF

(71) Applicant: Jilin University, Changchun (CN)

(72) Inventors: Xiaogang Zhao, Changchun (CN); Bing Cong, Changchun (CN); Hongwei Zhou, Changchun (CN); Daming Wang, Changchun (CN); Chunhai Chen, Changchun (CN)

(73) Assignee: JILIN UNIVERSITY, Changchun (CN)

( * ) Notice: Subject to any disclaimer, the term of this patent is extended or adjusted under 35 U.S.C. 154(b) by 0 days.

(21) Appl. No.: 18/086,530

(22) Filed: Dec. 21, 2022

(65) Prior Publication Data
US 2023/0405567 A1 Dec. 21, 2023

(30) Foreign Application Priority Data
Dec. 24, 2021 (CN) .......................... 202111600379.6

(51) Int. Cl.
*B01J 31/18* (2006.01)
*B01J 37/04* (2006.01)
*C08G 83/00* (2006.01)

(52) U.S. Cl.
CPC ............. *B01J 31/183* (2013.01); *B01J 37/04* (2013.01); *C08G 83/008* (2013.01)

(58) Field of Classification Search
CPC ........ B01J 31/183; B01J 37/04; C08G 83/008
See application file for complete search history.

(56) References Cited

FOREIGN PATENT DOCUMENTS

CN 101423757 A * 5/2009

OTHER PUBLICATIONS

CNIPA, Notification to grant patent right for invention in CN202111600379.6, Oct. 26, 2022.
Jilin University (Applicant), Original Claims (allowed) for invention in CN202111600379.6, Dec. 24, 2021.

* cited by examiner

*Primary Examiner* — Yong L Chu
(74) *Attorney, Agent, or Firm* — Zhigang Ma

(57) ABSTRACT

A polydentate organic ligand, a preparation method and an application method thereof, a metallo-supramolecular polymer and a preparation method thereof are provided. A structure of triphenylamine is combined with a structure of phenanthroline to serve as the polydentate organic ligand, which takes advantages of a large-volume distortion structure and excellent electroactivity of the triphenylamine. The polydentate organic ligands have good solubility, which provides lower-cost and diversified methods for preparing the metallo-supramolecular polymers. Meanwhile, the phenanthroline has a rigid structure and a conjugated large π bond in its molecule, which facilitates chelating coordination with metal ions to form a stable compound. Therefore, the polydentate organic ligand enables the metallo-supramolecular polymer to have good transferability, stable electroactivity, and high conversion speed, i.e., fast response speed, excellent electrochromic cycling stability and long service lifetime.

6 Claims, 4 Drawing Sheets

POLYDENTATE ORGANIC LIGAND, PREPARATION METHOD AND APPLICATION THEREOF, METALLO-SUPRAMOLECULAR POLYMER AND PREPARATION METHOD THEREOF

TECHNICAL FIELD

The disclosure belongs to a technical field of functional molecular materials, and in particular to a polydentate organic ligand, a preparation method and an application method thereof, a metallo-supramolecular polymer and a preparation method thereof.

BACKGROUND

Since a first electrochromic device has been reported from 1969, electrochromic materials have undergone several generations of development. For example, a first generation is metal oxides, such as tungsten trioxide, etc.; a second generation is transition metal complexes, such as ruthenium-bipyridine; and a third generation is organic molecules and conductive polymers, such as polythiophene. The first generation to the third generation in electrochromic materials is mainly applied in intelligent windows. In addition, they are also partly applied in optical display, anti-counterfeiting materials, mobile phone shells and information storage. Metallo-supramolecular polymers belong to a fourth generation, which are novel electrochromic materials formed by a complexation of metal ions and the polydentate organic ligand. The metallo-supramolecular polymers exhibit a reversible electrochromic behavior due to electrochemical redox of the metal ions triggering metal-ligand charge-transfer (MLCT), intensity change of d-d transition of the metal ions, or intervalence charge-transfer (IVCT). However, the current electrochromic materials prepared by the metallo-supramolecular polymers generally have disadvantages such as a slow response speed.

SUMMARY

An object of the disclosure is to provide a polydentate organic ligand, a preparation method and an application method thereof, a metallo-supramolecular polymer and a preparation method thereof. The metallo-supramolecular polymer prepared by the polydentate organic ligand has a fast response speed.

In order to achieve the above object, the disclosure provides technical solutions as follows.

The disclosure provides the polydentate organic ligand including a structure of triphenylamine-phenanthroline, and the structure of triphenylamine-phenanthroline is expressed by Formula I:

(Formula I)

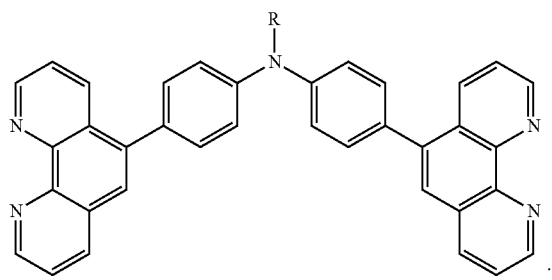

In the Formula I, R is one selected from a group consisting of compositions represented by following structures:

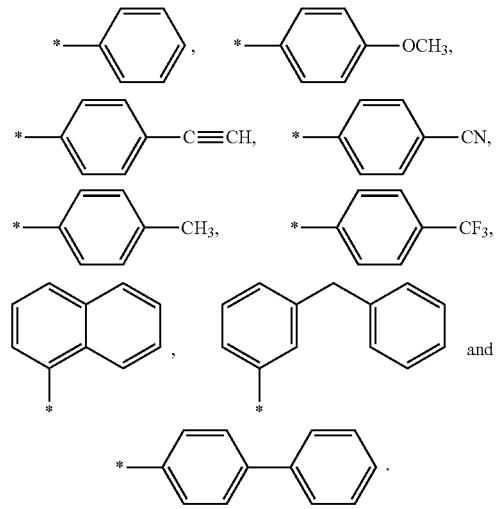

The disclosure provides a preparation method of the polydentate organic ligand including the structure of triphenylamine-phenanthroline in the above technical solution, including following steps:

mixing diphenylamine, N-bromosuccinimide and a first organic solvent to perform a bromination reaction, thereby to obtain a bis(4-bromophenyl)amine;

mixing the bis(4-bromophenyl)amine, an X-R compound, a first alkali, a first catalyst and a second organic solvent to perform a Ullmann reaction, thereby to obtain a dibromo compound;

mixing the dibromo compound, bis(pinacolato)diboron, a second alkali, a second catalyst, and a third organic solvent to perform a first Suzuki coupling reaction, thereby to obtain a triphenylamine pinacol borate ester compound (i.e., triphenylamine pinacol borate ester); and mixing the triphenylamine pinacol borate ester compound, 5-Br-phenanthroline, a third alkali, a third catalyst and a fourth organic solvent to perform a second Suzuki coupling reaction, thereby to obtain the polydentate organic ligand including the structure of triphenylamine-phenanthroline.

In the X-R compound, X is a halogen, and R is the one selected from the group consisting of the compositions represented by the following structures:

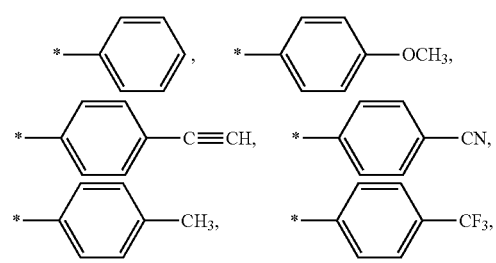

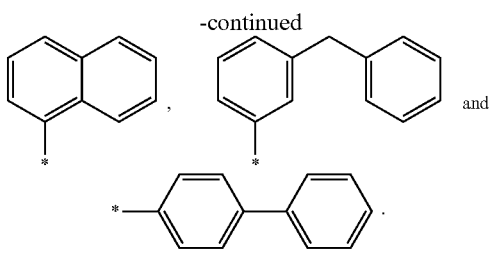, and

In an illustrated embodiment of the disclosure, a molar ratio of the diphenylamine:the N-bromosuccinimide is 1:(2-2.5); a temperature of the bromination reaction is room temperature, and a time of the bromination reaction is between 24 hours (h) and 36 h.

In an illustrated embodiment of the disclosure, the first alkali includes one selected from a group consisting of potassium hydroxide, sodium hydroxide, potassium carbonate, sodium carbonate and cesium carbonate; the first catalyst includes phenanthroline and cuprous iodide; a molar ratio of the bis(4-bromophenyl)amine:the X-R compound: the first alkali is 1:(1-1.5):(8-9); a molar ratio of the cuprous iodide:the phenanthroline is (0.03-0.05):(0.03-0.05); a molar ratio of the bis(4-bromophenyl)amine:the cuprous iodide is 1:(0.03-0.05); a temperature of the Ullmann reaction is between 110 degrees Celsius (° C.) and 120° C.; and a time of the Ullmann reaction is between 20 h and 30 h.

In an illustrated embodiment of the disclosure, the second alkali includes one selected from a group consisting of potassium acetate, sodium carbonate, lithium carbonate and potassium phosphate; the second catalyst includes [1,1'-bis(diphenylphosphino)ferrocene]dichloropalladium(II); a molar ratio of the dibromo compound:the bis(pinacolato)diboron:the second alkali:the second catalyst is 1:(2-2.5):(5-8):(0.03-0.05); a temperature of the Suzuki coupling reaction is between 110° C. and 120° C.; and a time of the first Suzuki coupling reaction is 12 h.

In an illustrated embodiment of the disclosure, the third alkali includes potassium carbonate; the third catalyst includes tetrakis(triphenylphosphine)palladium; a molar ratio of the triphenylamine pinacol borate ester compound: the 5-Br-phenanthroline:the third catalyst:the third alkali is 1:(2-2.5):(0.03-0.05):(5-8); a temperature of the second Suzuki coupling reaction is between 110° C. and 120° C.; and a time of the second Suzuki coupling reaction is 12 h.

The disclosure provides an application method of the polydentate organic ligand including the structure of triphenylamine-phenanthroline or the polydentate organic ligand including the structure of triphenylamine-phenanthroline prepared by the preparation method in the above technical solutions in an electrochromic field.

The disclosure provides a metallo-supramolecular polymer, polymerized by a polydentate organic ligand and metal salt. The polydentate organic ligand is the polydentate organic ligand including the structure of triphenylamine-phenanthroline or the polydentate organic ligand including the structure of triphenylamine-phenanthroline prepared by the preparation method in the above technical solutions.

The disclosure provides a preparation method of the metallo-supramolecular polymer in the above technical solution, including following steps:
mixing a solution of the polydentate organic ligand and an aqueous solution of the metal salt to polymerize, thereby to obtain the metallo-supramolecular polymer. And the polydentate organic ligand is the polydentate organic ligand including the structure of triphenylamine-phenanthroline or the polydentate organic ligand including the structure of triphenylamine-phenanthroline prepared by the preparation method in the above technical solutions.

In an illustrated embodiment of the disclosure, the metal salt includes one of $Fe(BF_4)_2 \cdot 6H_2O$, $Cu(ClO_4)_2 \cdot 6H_2O$, $Co(OAc)_2 \cdot 4H_2O$ and $Cd(ClO_4)_2 \cdot 6H_2O$; a concentration of the solution of the polydentate organic ligand is between $1 \times 10^{-4}$ mole per liter (mol/L) and $2 \times 10^{-4}$ mol/L, a concentration of the aqueous solution of the metal salt is between $1 \times 10^{-2}$ mol/L and $2 \times 10^{-2}$ mol/L; and a volume ratio of the solution of the polydentate organic ligand:the aqueous solution of the metal salt is 1:1.

The disclosure provides the polydentate organic ligand including the structure of triphenylamine-phenanthroline. In the disclosure, a structure of triphenylamine and a structure of phenanthroline are combined to serve as the polydentate organic ligand. The structure of triphenylamine is introduced into the polydentate organic ligand due to its bulk distorted structure and excellent electroactivity. Therefore, the polydentate organic ligands have good solubility, providing lower-cost and diversified methods for preparing the metallo-supramolecular polymers. And introducing the structure of triphenylamine can effectively attenuate build-up of polymer chain, speed up transport of electrolyte ions and improve conversion rate. Meanwhile, a plane rigid structure of the phenanthroline and a conjugated large π bond in its molecule enable the phenanthroline to chelate and coordinate with the metal ions extremely easily to form a stable compound. Therefore, the polydentate organic ligand provided by the disclosure enables the metallo-supramolecular polymer to have stable electrical activity, fast response speed, excellent electrochromic cycling stability and long lifetime.

The disclosure prepares the metallo-supramolecular polymer by liquid-liquid interface polymerization and coordination-driven self-assembly, which can directly obtain an electrochromic film between two incompatible phase interfaces. And the film can directly be transferred to any one kind of substrate (such as a silicon wafer or an indium tin oxide (ITO) glass) for testing and application. Furthermore, the metallo-supramolecular polymer has good transferability; there is no need to dissolve the film in the organic solvent again for spin coating; a thickness of the film obtained can be regulated by a time of the reaction; and a surface of the film is uniform and a process of preparing the film is simple.

DETAILED DESCRIPTION OF EMBODIMENTS

Figure 1:
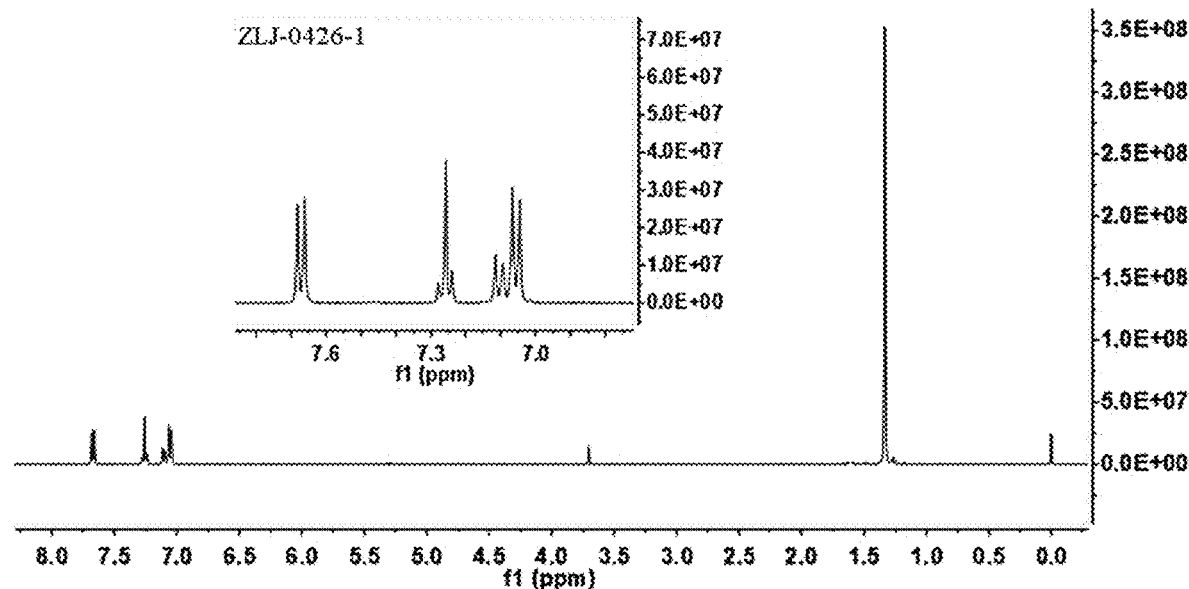
FIG. 1 illustrates a hydrogen nuclear magnetic resonance (NMR) spectrum of triphenylamine pinacol borate ester according to an embodiment 1 of the disclosure.

The disclosure provides a polydentate organic ligand including a structure of triphenylamine-phenanthrolinem, which is expressed by a Formula I as follows:

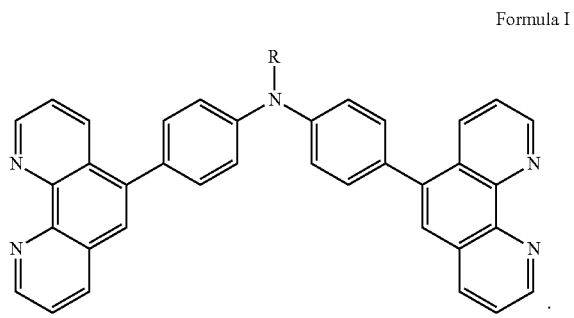

Formula I

In the Formula I, R is one selected from a group consisting of compositions represented by following structures:

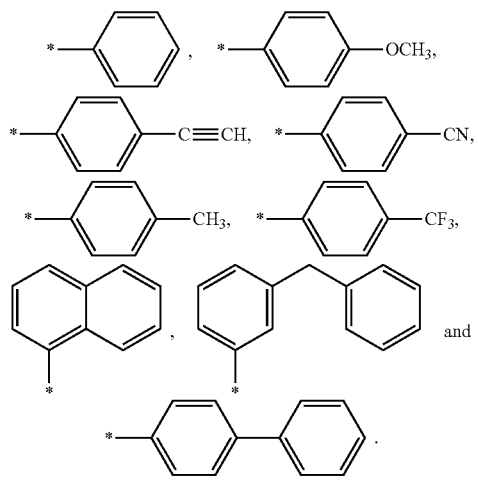

The disclosure provides a preparation method of the polydentate organic ligand including the structure of triphenylamine-phenanthrolinem described as the above technical solution, including following steps:

step 1) mixing diphenylamine, N-bromosuccinimide and a first organic solvent to perform a bromination reaction, thereby to obtain bis(4-bromophenyl)amine;

step 2) mixing the bis(4-bromophenyl)amine, an X-R compound, a first alkali, a first catalyst and a second organic solvent to perform a Ullmann reaction, thereby to obtain a dibromo compound;

step 3) mixing the dibromo compound, bis(pinacolato)diboron, a second alkali, a second catalyst and a third organic solvent to perform a first Suzuki coupling reaction, thereby to obtain a triphenylamine pinacol borate ester compound; and step 4) mixing the triphenylamine pinacol borate ester compound, 5-Br-phenanthroline, a third alkali, a third catalyst and a fourth organic solvent to perform a second Suzuki coupling reaction, thereby to obtain the polydentate organic ligand including the structure of triphenylamine-phenanthroline.

In the X-R compound, X is a halogen, and R is the one selected from the group consisting of the compositions represented by the following structures:

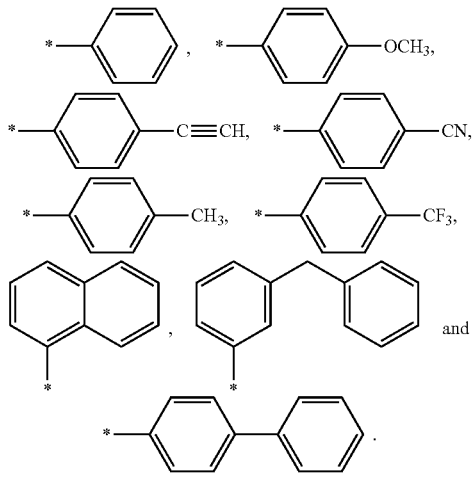

In the disclosure, raw materials required for the preparation method are commercially available commodities known to those skilled in the related art, if not otherwise specified.

In the disclosure, the diphenylamine, the N-bromosuccinimide and the first organic solvent are mixed to perform the bromination reaction, thereby the bis(4-bromophenyl)amine is obtained. In the disclosure, a molar ratio of the diphenylamine:the N-bromosuccinimide in step 1) is 1:(2-2.5); and in an illustrated embodiment of the disclosure, the molar ratio of the diphenylamine:the N-bromosuccinimide in step 1) is 1:(2.2-2.3). The first organic solvent is N, N-dimethylformamide (DMF).

In an illustrated embodiment of the disclosure, the process of mixing the diphenylamine, the N-bromosuccinimide and the first organic solvent to perform the bromination reaction includes: dissolving the diphenylamine in a part of the first organic solvent to obtain a diphenylamine solution; dissolving the N-bromosuccinimide in surplus of the first organic solvent to obtain an N-bromosuccinimide solution; and dropping the N-bromosuccinimide solution into the diphenylamine solution under a condition of ice-water cold bath. Concentrations of the diphenylamine solution and the N-bromosuccinimide solution are respectively 1 millimole per 0.8-1.01 milliliter (mmol/mL); and in an illustrated embodiment of the disclosure, the concentrations of the diphenylamine solution and the N-bromosuccinimide solution are 1 mmol/(0.81-0.88) mL.

In the disclosure, a temperature of the bromination reaction is room temperature; a time of the bromination reaction is between 24 hours (h) and 36 h; and in an illustrated embodiment of the disclosure, the time of the bromination reaction is between 30 h and 35 h. The bromination reaction is performed by stirring, which is not particularly limited, and is generated according to a process well known in the related art to ensure that the reaction proceeds smoothly.

After the bromination reaction, the first obtained material is discharged into the ice-water mixture for precipitation, and the obtained precipitate is filtered and dried under vacuum to obtain the bis(4-bromophenyl)amine. The processes of discharging, filtering and vacuum drying as described in the disclosure are not specifically limited, but are carried out according to the process known in the related art.

In the disclosure, taking the DMF being the first organic solvent as an example, the process of the bromination reaction is expressed by Formula 1 as follows:

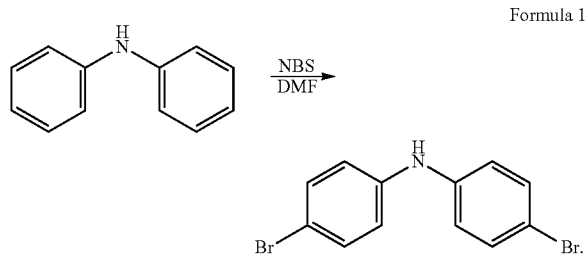

Formula 1

After obtaining the bis(4-bromophenyl)amine, the disclosure mixes the bis(4-bromophenyl)amine, the X-R compound, the first alkali, the first catalyst and the second organic solvent to perform the Ullmann reaction to obtain the dibromo compound. In the disclosure, X in the X-R compound is the halogen. In an illustrated embodiment of the disclosure, X is iodine (I), chlorine (Cl) or bromine (Br), and R is the one selected from the group consisting of the compositions represented by the following structures:

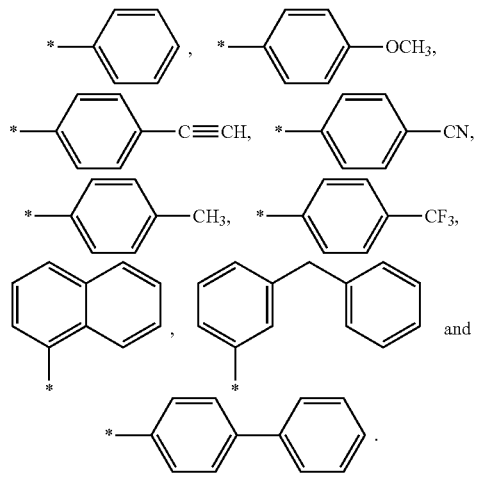

In the disclosure, the first alkali includes potassium hydroxide, sodium hydroxide, potassium carbonate, sodium carbonate or cesium carbonate; the first catalyst includes phenanthroline and cuprous iodide; and in an illustrated embodiment of the disclosure, the phenanthroline is 1,10-phenanthroline. In the disclosure, a molar ratio of the bis(4-bromophenyl)amine:the X-R compound:the first alkali is 1:(1-1.5):(8-9); and in an illustrated embodiment of the disclosure, the molar ratio of the bis(4-bromophenyl)amine: the X-R compound:the first alkali is 1:(1.2-1.3):(8.5-8.8). In the disclosure, a molar ratio of the cuprous iodide:the phenanthroline is (0.03-0.05):(0.03-0.05). In the disclosure, a molar ratio of the bis(4-bromophenyl)amine:the cuprous iodide is 1:(0.03-0.05); and in an illustrated embodiment of the disclosure, the molar ratio of the bis(4-bromophenyl) amine:the cuprous iodide is 1:(0.039-0.05).

In the disclosure, the second organic solvent is anhydrous toluene, and a dosage ratio of the bis(4-bromophenyl)amine: the second organic solvent is 1 mmol:(1-5) mL; and in an illustrated embodiment of the disclosure, the dosage ratio of the bis(4-bromophenyl)amine:the second organic solvent is 1 mmol:(2-3.2) mL.

In the disclosure, the process of mixing the bis(4-bromophenyl)amine, the X-R compound, the first alkali, the first catalyst and the second organic solvent includes: adding the X-R compound, the first alkali, the second organic solvent and the bis(4-bromophenyl) amine into a Schrank flask, and then applying three nitrogen-vacuum cycles, adding the first catalyst, and then applying another three nitrogen-vacuum cycles. The disclosure excludes oxygen from the reaction by applying the nitrogen-vacuum cycle.

In the disclosure, a temperature of the Ullmann reaction is between 110 degrees Celsius (° C.) and 120° C.; and in an illustrated embodiment of the disclosure, the temperature of the Ullmann reaction is 115° C. In the disclosure, a time of the Ullmann reaction is between 20 h and 30 h; and in an illustrated embodiment of the disclosure, the time of the Ullmann reaction is between 24 h and 25 h.

After the Ullmann reaction, the disclosure subjects a first reacted product for extraction, drying, rotatory evaporation and purification in sequence to obtain the dibromo compound.

In the disclosure, a reagent used in the extraction is dichloromethane and water, and a volume ratio of the dichloromethane:the water is 2:(1-2). There is no special limitation on the number of the extractions in the disclosure, which can be adjusted according to the actual demand. After the extraction, organic phases are combined and the first reacted product is dried; a reagent used for drying is anhydrous sodium sulfate. The process of the rotatory evaporation is not specially limited in the disclosure, but can be carried out according to the process known in the related art. In the disclosure, a method of the purification is column chromatography, and an eluent used in the column chromatography includes the dichloromethane and petroleum ether, and a volume ratio of the dichloromethane:the petroleum ether is (3-5):1.

In the disclosure, taking the 1,10-phenanthroline and cuprous iodide (also referred to CuI) being the first catalyst, the potassium hydroxide (also referred to KOH) being the first alkali, and the toluene being the second organic solvent as an example, the process of the Ullmann reaction is expressed by Formula 2 as follows:

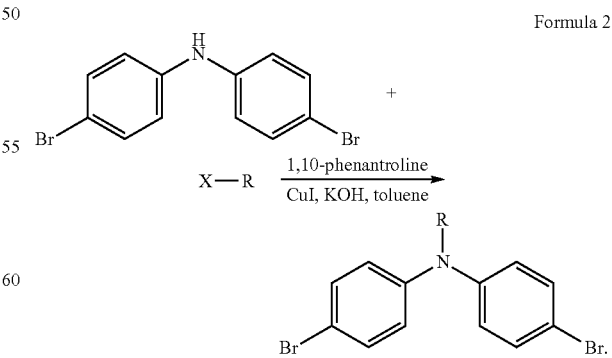

Formula 2

After obtaining the dibromo compound, the disclosure mixes the dibromo compound, the bis(pinacolato)diboron, the second alkali, the second catalyst and the third organic solvent to perform a first Suzuki coupling reaction to obtain the triphenylamine pinacolato borate ester compound. In the disclosure, the second alkali includes potassium acetate, sodium carbonate, lithium carbonate or potassium phosphate. In an illustrated embodiment of the disclosure, the second catalyst is [1,1'-bis(diphenylphosphino)ferrocene]dichloropalladium(II). A molar ratio of the dibromo compound:the bis(pinacolato)diboron:the second alkali:the second catalyst is 1:(2-2.5):(5-8):(0.03-0.05); and in an illustrated embodiment of the disclosure, the molar ratio of the dibromo compound:the bis(pinacolato)diboron:the second alkali:the second catalyst is 1:(2.39-2.4):(5-6):(0.038-0.05).

In the disclosure, the third organic solvent is 1,4-dioxane, and a dosage ratio of the dibromo compound:the third organic solvent is 1 mmol:10 mL.

In the disclosure, the process of mixing the dibromo compound, the bis(pinacolato)diboron, the second alkali, the second catalyst and the third organic solvent includes: adding the dibromo compound, the bis(pinacolato)diboron, the second alkali and the second catalyst into a Schrank flask, and then applying three nitrogen-vacuum cycles, adding the third organic solvent using a syringe, and then applying another three nitrogen-vacuum cycles.

In the disclosure, a temperature of the first Suzuki coupling reaction is between 110° C. and 120° C.; and in an illustrated embodiment of the disclosure, the temperature of the first Suzuki coupling reaction is 115° C. In the disclosure, a time of the first Suzuki coupling reaction is 12 h.

After the first Suzuki coupling reaction, the disclosure subjects the second reacted product for extraction, drying and rotatory evaporation in turn to obtain the triphenylamine pinacol borate ester compound. In the disclosure, the reagent used for the extraction includes dichloromethane and water, and a volume ratio of the dichloromethane:the water is 2:(1-2), and the reagent used for drying is anhydrous sodium sulfate. The disclosure has no special limitation on the process of the rotatory evaporation, and it is sufficient to follow the process known in the related art.

In the disclosure, taking the [1,1'-bis(diphenylphosphino)ferrocene]dichloropalladium(II) (also referred to Pd(dppf)Cl$_2$) being the second catalyst, the potassium acetate (also referred to KOAc) being the second alkali, and 1,4-dioxane being the third organic solvent as an example, the process of the first Suzuki coupling reaction is expressed by Formula 3 as follows:

Formula 3

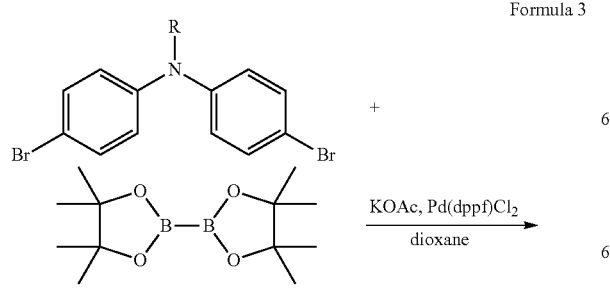

-continued

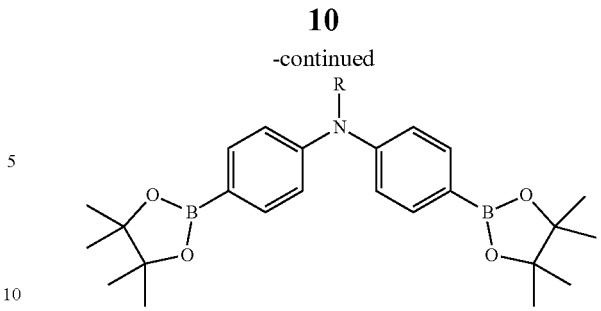

After obtaining the triphenylamine pinacol borate ester compound, the disclosure mixes the triphenylamine pinacol borate ester compound, the 5-Br-phenanthroline, the third alkali, the third catalyst and the fourth organic solvent to perform the second Suzuki coupling reaction to obtain the polydentate organic ligand including the structure of triphenylamine-phenanthroline. In the disclosure, the third alkali includes potassium carbonate, and the third catalyst includes tetrakis(triphenylphosphine)palladium; a molar ratio of the triphenylamine pinacol borate ester compound:the 5-Br-phenanthroline:the third catalyst:the third alkali is 1:(2-2.5):(0.03-0.05):(5-8); and in an illustrated embodiment of the disclosure, the molar ratio of the triphenylamine pinacol borate ester compound:the 5-Br-phenanthroline:the third catalyst:the third alkali is 1:2.3:(0.04-0.05):(6-7).

In the disclosure, the fourth organic solvent includes 1,4-dioxane and water, and a volume ratio of the 1,4-dioxane:the water is (3-3.5):1; and in an illustrated embodiment of the disclosure, the volume ratio of the 1,4-dioxane:the water is (3.2-3.5):1. A dosage ratio of the triphenylamine pinacol borate ester compound:the 1,4-dioxane is 1 mmol:10 mL.

In the disclosure, the process of mixing the triphenylamino pinacol borate ester compound, the 5-Br-phenanthroline, the third alkali, the third catalyst and the fourth organic solvent includes: adding the triphenylamino pinacol borate ester compound, the 5-Br-phenanthroline, the third alkali and the third catalyst into the Schrank flask, and then applying three nitrogen-vacuum cycles, and adding the fourth solvent using a syringe.

In the disclosure, a temperature of the second Suzuki coupling reaction is between 110° C. and 120° C.; and in an illustrated embodiment of the disclosure, the temperature of the second Suzuki coupling reaction is 115° C. In the disclosure, a time of the second Suzuki coupling reaction is 12 h.

After the second Suzuki coupling reaction, the disclosure discharges the second obtained material into deionized water for deionization, then dries the deionized material, and washes the dried material with methanol to obtain the polydentate organic ligand including the structure of triphenylamine-phenanthroline. The process of discharging, drying and washing is not particularly limited in the disclosure, but can be carried out according to the process known in the related art.

In the disclosure, taking the tetrakis(triphenylphosphine)palladium (also referred to Pd(pph$_4$)$_3$) being the third catalyst, the potassium carbonate (also referred to K$_2$CO$_3$) being the third alkali, and the 1,4-dioxane and the water being the fourth organic solvent, the process of the second Suzuki coupling reaction is expressed by Formula 4 as follows:

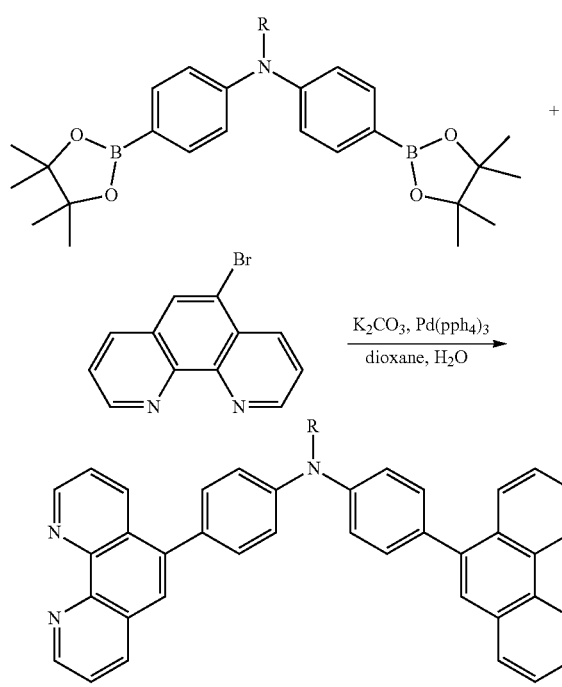

The disclosure provides an application method of the polydentate organic ligands including the structure of triphenylamine-phenanthroline or the polydentate organic ligand including the structure of triphenylamine-phenanthroline prepared by the preparation method described in the above technical solutions in an electrochromic field.

The disclosure provides a metallo-supramolecular polymer, which is polymerized by a polydentate organic ligand and metal salt. The polydentate organic ligand is the polydentate organic ligand including the structure of triphenylamine-phenanthroline or the polydentate organic ligand including the structure of triphenylamine-phenanthroline prepared by the preparation method described in the above technical solutions.

The disclosure provides a preparation method of the metallo-supramolecular polymer as described in the above technical solution, including following steps:
mixing a solution of the polydentate organic ligand and an aqueous solution of the metal salt to polymerize to obtain the metallo-supramolecular polymer. The polydentate organic ligand is the polydentate organic ligand including the structure of triphenylamine-phenanthroline or the polydentate organic ligand including the structure of triphenylamine-phenanthroline prepared by the preparation method described in the above technical solutions.

In the disclosure, the metal salt includes $Fe(BF_4)_2 \cdot 6H_2O$, $Cu(ClO_4)_2 \cdot 6H_2O$, $Co(OAc)_2 \cdot 4H_2O$ or $Cd(ClO_4)_2 \cdot 6H_2O$. In an illustrated embodiment of the disclosure, a solvent of the solution of the polydentate organic ligand is trichloromethane.

In the disclosure, a concentration of the solution of the polydentate organic ligand is $(1-2) \times 10^{-4}$ mol/L; and in an illustrated embodiment of the disclosure, the concentration of the solution of the polydentate organic ligand is $1.5 \times 10^{-4}$ mol/L. In the disclosure, a concentration of the aqueous solution of the metal salt is $(1-2) \times 10^{-2}$ mol/L; and in an illustrated embodiment of the disclosure, the concentration of the aqueous solution of the metal salt is $1.5 \times 10^{-4}$ mol/L.

In the disclosure, a volume ratio of the solution of the polydentate organic ligand:the aqueous solution of the metal salt is 1:1.

In the disclosure, the process of mixing the solution of the polydentate organic ligand and the aqueous solution of the metal salt solution includes: adding the solution of the polydentate organic ligand into a beaker with a diameter of 4.5 cm and dropping a same volume of the aqueous solution of the metal salt to a phase of the trichloromethane to obtain a liquid-liquid interface. The disclosure does not have special limitations on the process of the dropping, it is sufficient to follow the process known in the related art.

After the mixing process, the disclosure leaves the resulting mixture for 3 to 7 days (for polymerizing) to form a thin film at the liquid-liquid interface; the thin film is transferred to a substrate; the substrate is rinsed with water and trichloromethane in turn to remove unreacted reagents; the thin film is dried to obtain the metallo-supramolecular polymer. In an illustrated embodiment of the disclosure, the substrate is an indium tin oxide (ITO) substrate; there is no special limitation on the process of the rinsing and drying in the disclosure, and it is sufficient to follow the process well known in the related art. In the disclosure, the metallo-supramolecular polymer is present on the surface of the ITO substrate in a form of thin film, which is easy to detect.

The disclosure does not have a special limit to a thickness of the thin film formed by the metallo-supramolecular polymer on the substrate, which is adjusted according to the actual demand.

The technical solutions in the disclosure will be clearly and completely described below in connection with the embodiments of the disclosure. Apparently, the described embodiments are only some of the embodiments of the disclosure, and not all of the embodiments of the disclosure. Based on the embodiments in the disclosure, all other embodiments obtained by those skilled in the field without creative labor are within the scope of the protection of the disclosure. All other embodiments obtained by those skilled in the technical field without creative work are within the scope of the protection of the disclosure.

Embodiment 1

A structure of the polydentate organic ligand 1 is expressed by a structural formula as follows:

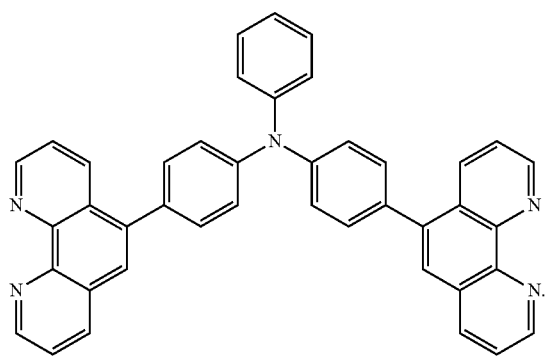 [SMILES: c1ccc(N(c2ccc(-c3cc4cccnc4c4ncccc34)cc2)c2ccc(-c3cc4cccnc4c4ncccc34)cc2)cc1]

(1) 5 grams (g) (also equal to 29.6 millimoles (mmol)) of diphenylamine is dissolved in 30 milliliters (mL) of N, N-dimethylformamide under the condition of ice-water cold bath to obtain a N, N-dimethylformamide solution of diphenylamine; 10 g (also equal to 59.2 mmol) of N-bromosuccinimide (NBS) is dissolved in 60 mL of the N, N-dimethylformamide to obtain a N, N-dimethylformamide solution of NBS, and the N, N-dimethylformamide solution of NBS is dropped into the N, N-dimethylformamide solution of diphenylamine to obtain a first mixing solution; the first mixing solution is stirred at room temperature for 24 h to perform a bromination reaction; the obtained first material is discharged into the ice-water mixture for precipitation after the bromination reaction; and then the precipitate is filtered and dried under vacuum to obtain 7.8 g of bis(4-bromophenyl)amine, which illustrates a yield of 81.3%.

(2) 2.4 g (also equal to 12.0 mmol) of iodobenzene, 4.12 g (also equal to 73.6 mmol) of potassium hydroxide, 30 mL of anhydrous toluene and 3 g (also equal to 9.2 mmol) of the bis(4-bromophenyl)amine are added into a first Schrank flask, and then applying three nitrogen-vacuum cycles to obtain a second mixing solution; 49.7 milligrams (mg) (also equal to 0.28 mmol) 1,10-phenanthroline and 53.3 mg (also equal to 0.28 mmol) cuprous iodide are added into the second mixing solution, and then applying another three nitrogen-vacuum cycles to obtain a third mixing solution, and the third mixing solution is heated to 110° C. to perform a Ullmann reaction for 24 h to obtain a first reacted product; dichloromethane and water are used to extract the first reacted product for three times after the Ullmann reaction, each time of the extraction uses 10 mL of the dichloromethane and 20 mL of the water to combine organic phases to obtain a first extracted product; the first extracted product is dried with anhydrous sodium sulfate to obtain a first dried product; the first dried product is purified by column chromatography after a rotary evaporation; an eluent of the column chromatography includes the dichloromethane and petroleum ether, and a volume ratio of the dichloromethane: the petroleum ether is 3:1, and 2.5 g of 4,4'-dibromotriphenylamine is obtained, which illustrates a yield of 67.8%.

(3) 2 g (also equal to 4.96 mmol) of the 4,4'-dibromotriphenylamine, 3.02 g (also equal to 11.9 mmol) of bis(pinacolato)diboron, 2.43 g (also equal to 24.8 mmol) of potassium acetate and 181.5 mg (also equal to 0.248 mmol) of [1,1'-bis(diphenylphosphino)ferrocene]dichloropalladium(II) are added to a second Schrank flask, and then applying three nitrogen-vacuum cycles to obtain a first mixture; the first mixture is added with 49.6 mL of 1,4-dioxane served as a solvent by using a syringe, and then applying another three nitrogen-vacuum cycles to obtain a fourth mixing solution, and the fourth mixing solution performs a first Suzuki coupling reaction in 110° C. for 12 h to obtain a second reacted product; the dichloromethane (3*10 mL) and the water (20 mL) are used to extract the second reacted product and combine the organic phases after the first Suzuki coupling reaction to obtain a second extracted product, and the second extracted product is dried with the anhydrous sodium sulfate; and then 2.16 g of triphenylamine pinacol borate ester is obtained after the rotatory evaporation, which illustrates a yield of 84%.

(4) 1.5 g (also equal to 3 mmol) of the triphenylamine pinacol borate ester, 1.8 g (also equal to 6.9 mmol) of 5-Br-phenanthroline, 104 mg (also equal to 0.09 mmol) of tetrakis(triphenylphosphine)palladium and 2.07 g (15 mmol) of potassium carbonate are added into a third Schrank flask, and then applying three nitrogen-vacuum cycles to obtain a second mixture; the second mixture is added with 30 mL of the 1,4-dioxane and 10 mL of the water by using a syringe to obtain a fifth mixing solution, and the fifth mixing solution performs a second Suzuki coupling reaction in 110° C. for 12 h; the obtained second material is added into deionized water for deionization after the second Suzuki coupling reaction, then the deionized material is dried, and the dried material is washed with methanol to obtain 1.2 g of a target ligand 1, which illustrates a yield of 67%.

Embodiment 2

A structure of the polydentate organic ligand 2 is expressed by a structural formula as follows:

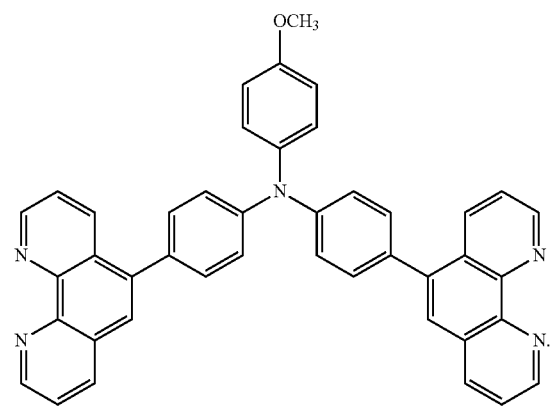 [SMILES: COc1ccc(N(c2ccc(-c3cc4cccnc4c4ncccc34)cc2)c2ccc(-c3cc4cccnc4c4ncccc34)cc2)cc1]

(1) 5 g (also equal to 29.6 mmol) of diphenylamine is dissolved in 30 mL of N, N-dimethylformamide under the condition of ice-water cold bath to obtain a N, N-dimethylformamide solution of diphenylamine; 12.12 g (also equal to 68.1 mmol) of NBS is dissolved in 60 mL of the N, N-dimethylformamide to obtain a N, N-dimethylformamide solution of NBS, and the N, N-dimethylformamide solution of NBS is dropped to the N, N-dimethylformamide solution of diphenylamine to obtain a first mixing solution; the first mixing solution is stirred at room temperature for 30 h to perform a bromination reaction; the obtained first material is discharged into the ice-water mixture for precipitation after the bromination reaction; and then the precipitate is filtered and dried under vacuum to obtain 7.6 g of bis(4-bromophenyl)amine, which illustrates a yield of 79%.

(2) 3.23 g (also equal to 13.8 mmol) of p-iodoanisole, 4.65 g (also equal to 82.8 mmol) of potassium hydroxide, 30 mL of anhydrous toluene and 3 g (also equal to 9.2 mmol) of the bis(4-bromophenyl)amine are added into a first Schrank flask, and then applying three nitrogen-vacuum cycles to obtain a second mixing solution; 82.9 mg (also equal to 0.46 mmol) 1,10-phenanthroline and 87.6 mg (also equal to 0.46 mmol) cuprous iodide are added into the second mixing solution, and then applying another three nitrogen-vacuum cycles to obtain a third mixing solution, and the third mixing solution is heated to 120° C. to perform a Ullmann reaction for 30 h to obtain a first reacted product; dichloromethane and water are used to extract the first reacted product for three times after the Ullmann reaction, each time of the extraction uses 10 mL of the dichloromethane and 20 mL of the water to combine organic phases to obtain a first extracted product; the first extracted product is dried with anhydrous sodium sulfate to obtain a first dried product; the first dried product is purified by column chromatography after a rotary evaporation; an eluent of the column chromatography includes the dichloromethane and petroleum ether, and a volume ratio of the dichloromethane:the petroleum ether is 5:1, and 2.37 g of 4-methoxy-4',4"-dibromotriphenylamine is obtained, which illustrates a yield of 59.5%.

(3) 2.15 g (also equal to 4.96 mmol) of the 4-methoxy-4',4''-dibromotriphenylamine, 2.52 g (also equal to 9.92 mmol) of bis(pinacolato)diboron, 3.89 g (also equal to 39.7 mmol) of potassium acetate and 108.9 mg (also equal to 0.149 mmol) of [1,1'-bis(diphenylphosphino)ferrocene]dichloropalladium(II) are added to a second Schrank flask, and then applying three nitrogen-vacuum cycles to obtain a first mixture; the first mixture is added with 49.6 mL of 1,4-dioxane served as a solvent by using a syringe, and then applying another three nitrogen-vacuum cycles to obtain a fourth mixing solution, and the fourth mixing solution performs a first Suzuki coupling reaction in 120° C. for 12 h to obtain a second reacted product; the dichloromethane (3*10 mL) and the water (20 mL) are used to extract the second reacted product and combine the organic phases after the first Suzuki coupling reaction to obtain a second extracted product, and the second extracted product is dried with the anhydrous sodium sulfate; and then 2.08 g of 4-methoxytriphenylamine pinacol borate ester is obtained after the rotatory evaporation, which illustrates a yield of 79.4%.

(4) 1.58 g (also equal to 3 mmol) of the 4-methoxytriphenylamine pinacol borate ester, 1.55 g (also equal to 6 mmol) of 5-Br-phenanthroline, 173.3 mg (also equal to 0.15 mmol) of tetrakis(triphenylphosphine)palladium and 3.32 g (24 mmol) of potassium carbonate are added into a third Schrank flask, and then applying three nitrogen-vacuum cycles to obtain a second mixture; the second mixture is added with 30 mL of the 1,4-dioxane and 10 mL of the water by using a syringe to obtain a fifth mixing solution, and the fifth mixing solution performs a second Suzuki coupling reaction in 120° C. for 12 h to obtain a second material; the obtained second material is added into deionized water for deionization after the second Suzuki coupling reaction, then the deionized material is dried, and the dried material is washed with methanol to obtain 1.35 g of a target ligand 2, which illustrates a yield of 68%.

Embodiment 3

A structure of the polydentate organic ligand 3 is expressed by a structural formula as follows:

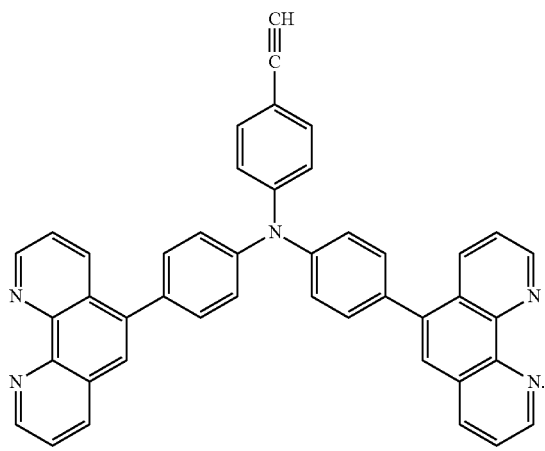 [SMILES: C#Cc1ccc(N(c2ccc(-c3cc4cccnc4c4ncccc34)cc2)c2ccc(-c3cc4cccnc4c4ncccc34)cc2)cc1]

(1) 5 g (also equal to 29.6 mmol) of diphenylamine is dissolved in 30 mL of N, N-dimethylformamide under the condition of ice-water cold bath obtain a N, N-dimethylformamide solution of diphenylamine; 13.17 g (also equal to 74 mmol) of NBS is dissolved in 60 mL of the N, N-dimethylformamide to obtain a N, N-dimethylformamide solution of NBS, and the N, N-dimethylformamide solution of NBS is dropped to the N, N-dimethylformamide solution of diphenylamine to obtain a first mixing solution; the first mixing solution is stirred at room temperature for 36 h to perform a bromination reaction; the obtained first material is discharged into the ice-water mixture for precipitation after the bromination reaction; and then the precipitate is filtered and dried under vacuum to obtain 8.1 g of bis(4-bromophenyl)amine, which illustrates a yield of 83%.

(2) 3.23 g (also equal to 9.2 mmol) of 4-iodophenylacetylene, 4.39 g (also equal to 78.2 mmol) of potassium hydroxide, 30 mL of anhydrous toluene and 3 g (also equal to 9.2 mmol) of the bis(4-bromophenyl)amine are added into a first Schrank flask, and then applying three nitrogen-vacuum cycles to obtain a second mixing solution; 64.87 mg (also equal to 0.36 mmol) 1,10-phenanthroline and 68.56 mg (also equal to 0.36 mmol) cuprous iodide are added into the second mixing solution, and then applying another three nitrogen-vacuum cycles to obtain a third mixing solution, and the third mixing solution is heated to 115° C. to perform a Ullmann reaction for 25 h to obtain a first reacted product; dichloromethane and water are used to extract the first reacted product for three times after the Ullmann reaction, each time of the extraction uses 10 mL of the dichloromethane and 20 mL of the water to combine organic phases to obtain a first extracted product; the first extracted product is dried with anhydrous sodium sulfate to obtain a first dried product; the first dried product is purified by column chromatography after a rotary evaporation; an eluent of the column chromatography includes the dichloromethane and petroleum ether, and a volume ratio of the dichloromethane: the petroleum ether is 4:1, and 2.43 g of 4-alkynyl-4',4''-dibromotriphenylamine is obtained, which illustrates a yield of 61%.

(3) 2.15 g (also equal to 4.96 mmol) of the 4-alkynyl-4',4''-dibromotriphenylamine, 3.15 g (also equal to 12.4 mmol) of bis(pinacolato)diboron, 2.92 g (also equal to 29.8 mmol) of potassium acetate and 139.02 mg (also equal to 0.19 mmol) of [1,1'-bis(diphenylphosphino)ferrocene]dichloropalladium(II) are added to a second Schrank flask, and then applying three nitrogen-vacuum cycles to obtain a first mixture; the first mixture is added with 49.6 mL of 1,4-dioxane served as a solvent by using a syringe, and then applying another three nitrogen-vacuum cycles to obtain a fourth mixing solution, and the fourth mixing solution performs a first Suzuki coupling reaction in 115° C. for 12 h to obtain a second reacted product; the dichloromethane (3*10 mL) and the water (20 mL) are used to extract the second reacted product and combine the organic phases after the first Suzuki coupling reaction to obtain a second extracted product, and the second extracted product is dried with the anhydrous sodium sulfate; and then 1.96 g of 4-alkynyltriphenylamine pinacol borate ester is obtained after the rotatory evaporation, which illustrates a yield of 75%.

(4) 1.56 g (also equal to 3 mmol) of the 4-alkynyltriphenylamine pinacol borate ester, 1.94 g (also equal to 7.5 mmol) of 5-Br-phenanthroline, 138.7 mg (also equal to 0.12 mmol) of tetrakis(triphenylphosphine)palladium and 2.49 g (18 mmol) of potassium carbonate are added into a third Schrank flask, and then applying three nitrogen-vacuum cycles to obtain a second mixture; the second mixture is added with 30 mL of the 1,4-dioxane and 10 mL of the water by using a syringe to obtain a fifth mixing solution, and the fifth mixing solution performs a second Suzuki coupling reaction in 115° C. for 12 h to obtain a second material; the obtained second material is added into deionized water for deionization after the second Suzuki coupling reaction, then the deionized material is dried, and the dried material is washed with methanol to obtain 1.24 g of a target ligand 3, which illustrates a yield of 65%.

Embodiment 4

A structure of the polydentate organic ligand 4 is expressed by a structural formula as follows:

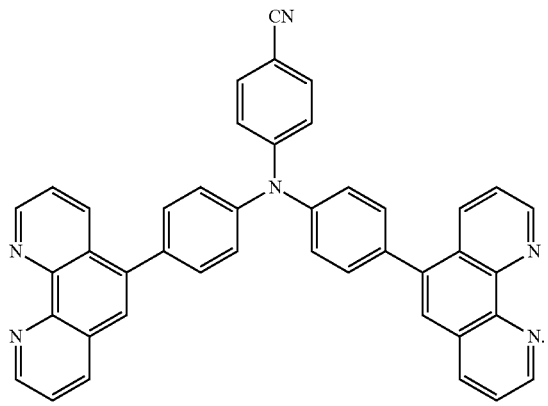 [SMILES: N#Cc1ccc(N(c2ccc(-c3cc4cccnc4c4ncccc34)cc2)c2ccc(-c3cc4cccnc4c4ncccc34)cc2)cc1]

(1) 5 g (also equal to 29.6 mmol) of diphenylamine is dissolved in 30 mL of N, N-dimethylformamide under the condition of ice-water cold bath to obtain a N, N-dimethylformamide solution of diphenylamine; 10 g (also equal to 59.2 mmol) of NBS is dissolved in 60 mL of the N, N-dimethylformamide to obtain a N, N-dimethylformamide solution of NBS, and the N, N-dimethylformamide solution of NBS is dropped to the N, N-dimethylformamide solution of diphenylamine to obtain a first mixing solution; the first mixing solution is stirred at room temperature for 24 h to perform a bromination reaction; the obtained first material is discharged into the ice-water mixture for precipitation after the bromination reaction; and then the precipitate is filtered and dried under vacuum to obtain 8.65 g of bis(4-bromophenyl)amine, which illustrates a yield of 89%.

(2) 2.74 g (also equal to 11.96 mmol) of 4-iodobenzonitrile, 4.13 g (also equal to 73.6 mmol) of potassium hydroxide, 30 mL of anhydrous toluene and 3 g (also equal to 9.2 mmol) of the bis(4-bromophenyl)amine are added into a first Schrank flask, and then applying three nitrogen-vacuum cycles to obtain a second mixing solution; 82.9 mg (also equal to 0.46 mmol) 1,10-phenanthroline and 87.61 mg (also equal to 0.46 mmol) cuprous iodide are added into the second mixing solution, and then applying another three nitrogen-vacuum cycles to obtain a third mixing solution, and the third mixing solution is heated to 110° C. to perform a Ullmann reaction for 24 h to obtain a first reacted product; dichloromethane and water are used to extract the first reacted product for three times after the Ullmann reaction, each time of the extraction uses 10 mL of the dichloromethane and 20 mL of the water to combine organic phases to obtain a first extracted product; the first extracted product is dried with anhydrous sodium sulfate to obtain a first dried product; the first dried product is purified by column chromatography after a rotary evaporation; an eluent of the column chromatography includes the dichloromethane and petroleum ether, and a volume ratio of the dichloromethane: the petroleum ether is 4:1, and 2.85 g of 4-cyano-4',4''-dibromotriphenylamine is obtained, which illustrates a yield of 73%.

(3) 2.12 g (also equal to 4.96 mmol) of the 4-cyano-4', 4''-dibromotriphenylamine, 3.02 g (also equal to 11.91 mmol) of bis(pinacolato)diboron, 2.43 g (also equal to 24.8 mmol) of potassium acetate and 182.93 mg (also equal to 0.25 mmol) of [1,1'-bis(diphenylphosphino)ferrocene]dichloropalladium(II) are added to a second Schrank flask, and then applying three nitrogen-vacuum cycles to obtain a first mixture; the first mixture is added with 49.6 mL of 1,4-dioxane served as a solvent by using a syringe, and then applying another three nitrogen-vacuum cycles to obtain a fourth mixing solution, and the fourth mixing solution performs a first Suzuki coupling reaction in 110° C. for 12 h to obtain a second reacted product; the dichloromethane (3*10 mL) and the water (20 mL) are used to extract the second reacted product and combine the organic phases after the first Suzuki coupling reaction to obtain a second extracted product, and the second extracted product is dried with the anhydrous sodium sulfate; and then 2.22 g of 4-cyanotriphenylamine pinacol borate ester is obtained after the rotatory evaporation, which illustrates a yield of 86%.

(4) 1.57 g (also equal to 3 mmol) of the 4-cyanotriphenylamine pinacol borate ester, 1.79 g (also equal to 6.9 mmol) of 5-Br-phenanthroline, 173.34 mg (also equal to 0.15 mmol) of tetrakis(triphenylphosphine)palladium and 2.07 g (15 mmol) of potassium carbonate are added into a third Schrank flask, and then applying three nitrogen-vacuum cycles to obtain a second mixture; the second mixture is added with 30 mL of the 1,4-dioxane and 10 mL of the water by using a syringe to obtain a fifth mixing solution, and the fifth mixing solution performs a second Suzuki coupling reaction in 110° C. for 12 h to obtain a second material; the obtained second material is added into deionized water for deionization after the second Suzuki coupling reaction, then the deionized material is dried, and the dried material is washed with methanol to obtain 1.37 g of a target ligand 4, which illustrates a yield of 73%.

Embodiment 5

A structure of the polydentate organic ligand 5 is expressed by a structural formula as follows:

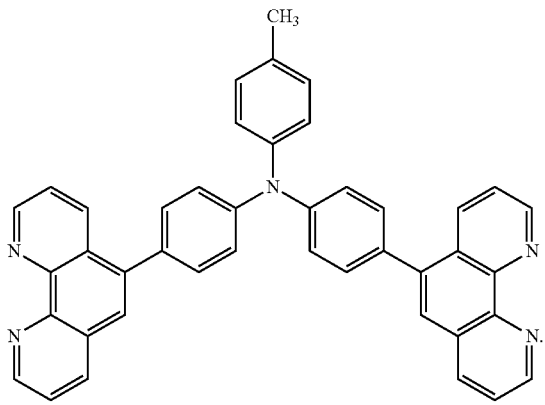 [SMILES: FC(F)(F)c1ccc(N(c2ccc(-c3cc4cccnc4c4ncccc34)cc2)c2ccc(-c3cc4cccnc4c4ncccc34)cc2)cc1]

(1) 5 g (also equal to 29.6 mmol) of diphenylamine is dissolved in 30 mL of N, N-dimethylformamide under the condition of ice-water cold bath to obtain a N, N-dimethylformamide solution of diphenylamine; 12.12 g (also equal to 68.08 mmol) of NBS is dissolved in 60 mL of the N, N-dimethylformamide to obtain a N, N-dimethylformamide solution of NBS, and the N, N-dimethylformamide solution of NBS is dropped to the N, N-dimethylformamide solution of diphenylamine to obtain a first mixing solution; the first mixing solution is stirred at room temperature for 24 h to perform a bromination reaction; the first obtained mixture is discharged into the ice-water mixture for precipitation after the bromination reaction; and then the precipitate is filtered and dried under vacuum to obtain 8.65 g of bis(4-bromophenyl)amine, which illustrates a yield of 89%.

(2) 2.61 g (also equal to 11.96 mmol) of 4-iodotoluene, 4.13 g (also equal to 73.6 mmol) of potassium hydroxide, 30 mL of anhydrous toluene and 3 g (also equal to 9.2 mmol) of the bis(4-bromophenyl)amine are added into a first Schrank flask, and then applying three nitrogen-vacuum cycles to obtain a second mixing solution; 82.9 mg) (also equal to 0.46 mmol) 1,10-phenanthroline and 87.61 mg (also equal to 0.46 mmol) cuprous iodide are added into the second mixing solution, and then applying another three nitrogen-vacuum cycles to obtain a third mixing solution, and the third mixing solution is heated to 110° C. to perform a Ullmann reaction for 24 h to obtain a first reacted product; dichloromethane and water are used to extract the first reacted product for three times after the Ullmann reaction, each time of the extraction uses 10 mL of the dichloromethane and 20 mL of the water to combine organic phases to obtain a first extracted product; the first extracted product is dried with anhydrous sodium sulfate to obtain a first dried product; the first dried product is purified by column chromatography after a rotary evaporation; an eluent of the column chromatography includes the dichloromethane and petroleum ether, and a volume ratio of the dichloromethane: the petroleum ether is 3:1, and 2.89 g of 4-methyl-4',4"-dibromotriphenylamine is obtained, which illustrates a yield of 76%.

(3) 2.07 g (also equal to 4.96 mmol) of the 4-methyl-4', 4"-dibromotriphenylamine, 3.02 g (also equal to 11.91 mmol) of bis(pinacolato)diboron, 2.43 g (also equal to 24.8 mmol) of potassium acetate and 182.93 mg (also equal to 0.25 mmol) of [1,1'-bis(diphenylphosphino)ferrocene]dichloropalladium(II) are added to a second Schrank flask, and then applying three nitrogen-vacuum cycles to obtain a first mixture; the first mixture is added with 49.6 mL of 1,4-dioxane served as a solvent by using a syringe, and then applying another three nitrogen-vacuum cycles to obtain a fourth mixing solution, and the fourth mixing solution performs a first Suzuki coupling reaction in 110° C. for 12 h to obtain a second reacted product; the dichloromethane (3*10 mL) and the water (20 mL) are used to extract the second reacted product and combine the organic phases after the first Suzuki coupling reaction to obtain a second extracted product, and the second extracted product is dried with the anhydrous sodium sulfate; and then 2.27 g of 4-methyltriphenylamine pinacol borate ester is obtained after the rotatory evaporation, which illustrates a yield of 90%.

(4) 1.53 g (also equal to 3 mmol) of the 4-methyltriphenylamine pinacol borate ester, 1.79 g (also equal to 6.9 mmol) of 5-Br-phenanthroline, 173.34 mg (also equal to 0.15 mmol) of tetrakis(triphenylphosphine)palladium and 2.07 g (15 mmol) of potassium carbonate are added into a third Schrank flask, and then applying three nitrogen-vacuum cycles to obtain a second mixture; the second mixture is added with 30 mL of the 1,4-dioxane and 10 mL of the water by using a syringe to obtain a fifth mixing solution, and the fifth mixing solution performs a second Suzuki coupling reaction in 110° C. for 12 h to obtain a second material; the obtained second material is added into deionized water for deionization after the second Suzuki coupling reaction, then the deionized material is dried, and the dried material is washed with methanol to obtain 1.59 g of a target ligand 5, which illustrates a yield of 86%.

Embodiment 6

A structure of the polydentate organic ligand 6 is expressed by a structural formula as follows:

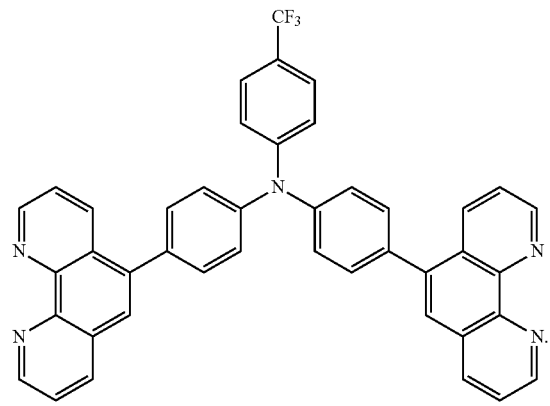

(1) 5 g (also equal to 29.6 mmol) of diphenylamine is dissolved in 30 mL of N, N-dimethylformamide the first obtained mixture is discharged into the ice-water mixture for precipitation to obtain a N, N-dimethylformamide solution of diphenylamine; 12.12 g (also equal to 68.08 mmol) of NBS is dissolved in 60 mL of the N, N-dimethylformamide to obtain a N, N-dimethylformamide solution of NBS, and the N, N-dimethylformamide solution of NBS is dropped to the N, N-dimethylformamide solution of diphenylamine to obtain a first mixing solution; the first mixing solution is stirred at room temperature for 24 h to perform a bromination reaction; the first obtained material is discharged into the ice-water mixture for precipitation after the bromination reaction; and then the precipitate is filtered and dried under vacuum to obtain 8.65 g of bis(4-bromophenyl)amine, which illustrates a yield of 89%.

(2) 3.25 g (also equal to 11.96 mmol) of 4-iodotrifluorotoluene, 4.13 g (also equal to 73.6 mmol) of potassium hydroxide, 30 mL of anhydrous toluene and 3 g (also equal to 9.2 mmol) of the bis(4-bromophenyl)amine are added into a first Schrank flask, and then applying three nitrogen-vacuum cycles to obtain a second mixing solution; 82.9 mg (also equal to 0.46 mmol) 1,10-phenanthroline and 87.61 mg (also equal to 0.46 mmol) cuprous iodide are added into the second mixing solution, and then applying another three nitrogen-vacuum cycles to obtain a third mixing solution, and the third mixing solution is heated to 110° C. to perform a Ullmann reaction for 24 h to obtain a first reacted product; dichloromethane and water are used to extract the first reacted product for three times after the Ullmann reaction, each time of the extraction uses 10 mL of the dichloromethane and 20 mL of the water to combine organic phases to obtain a first extracted product; the first extracted product is dried with anhydrous sodium sulfate to obtain a first dried product; the first dried product is purified by column chromatography after a rotary evaporation; an eluent of the column chromatography includes the dichloromethane and petroleum ether, and a volume ratio of the dichloromethane: the petroleum ether is 3:1, and 2.89 g of 4-trifluoromethyl-4',4"-dibromotriphenylamine is obtained, which illustrates a yield of 65%.

(3) 2.41 g (also equal to 4.96 mmol) of the 4-trifluoromethyl-4',4"-dibromotriphenylamine, 3.02 g (also equal to 11.91 mmol) of bis(pinacolato)diboron, 2.43 g (also equal to 24.8 mmol) of potassium acetate and 182.93 mg (also equal to 0.25 mmol) of [1,1'-bis(diphenylphosphino)ferrocene]dichloropalladium(II) are added to a second Schrank flask, and then applying three nitrogen-vacuum cycles to obtain a first mixture; the first mixture is added with 49.6 mL of 1,4-dioxane served as a solvent by using a syringe, and then applying another three nitrogen-vacuum cycles to obtain a fourth mixing solution, and the fourth mixing solution performs a first Suzuki coupling reaction in 110° C. for 12 h to obtain a second reacted product; the dichloromethane (3*10 mL) and the water (20 mL) are used to extract the second reacted product and combine the organic phases after the first Suzuki coupling reaction to obtain a second extracted product, and the second extracted product is dried with the anhydrous sodium sulfate; and then 2.37 g of 4-trifluoromethylphenylamine pinacol borate ester is obtained after the rotatory evaporation, which illustrates a yield of 85%.

(4) 1.7 g (also equal to 3 mmol) of the 4-trifluoromethylphenylamine pinacol borate ester, 1.79 g (also equal to 6.9 mmol) of 5-Br-phenanthroline, 173.34 mg (also equal to 0.15 mmol) of tetrakis(triphenylphosphine)palladium and 2.07 g (15 mmol) of potassium carbonate are added into a third Schrank flask, and then applying three nitrogen-vacuum cycles to obtain a second mixture; the second mixture is added with 30 mL of the 1,4-dioxane and 10 mL of the water by using a syringe to obtain a fifth mixing solution, and the fifth mixing solution performs a second Suzuki coupling reaction in 110° C. for 12 h to obtain a second material; the obtained second material is added into deionized water for deionization after the second Suzuki coupling reaction, then the deionized material is dried, and the dried material is washed with methanol to obtain 1.65 g of a target ligand 6, which illustrates a yield of 82%.

Embodiment 7

A structure of the polydentate organic ligand 7 is expressed by a structural formula as follows:

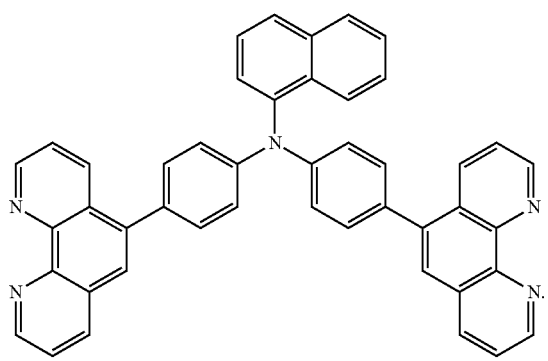 [SMILES: c1ccc2c(N(c3ccc(-c4cc5cccnc5c5ncccc45)cc3)c3ccc(-c4cc5cccnc5c5ncccc45)cc3)cccc2c1]

(1) 5 g (also equal to 29.6 mmol) of diphenylamine is dissolved in 30 mL of N, N-dimethylformamide the first obtained mixture is discharged into the ice-water mixture for precipitation to obtain a N, N-dimethylformamide solution of diphenylamine; 12.12 g (also equal to 68.08 mmol) of NBS is dissolved in 60 mL of the N, N-dimethylformamide to obtain a N, N-dimethylformamide solution of NBS, and the N, N-dimethylformamide solution of NBS is dropped to the N, N-dimethylformamide solution of diphenylamine to obtain a first mixing solution; the first mixing solution is stirred at room temperature for 24 h to perform a bromination reaction; the first obtained material is discharged into the ice-water mixture for precipitation after the bromination reaction; and then the precipitate is filtered and dried under vacuum to obtain 8.65 g of bis(4-bromophenyl)amine, which illustrates a yield of 89%.

(2) 2.48 g (also equal to 11.96 mmol) of 1-bromonaphthalene, 4.13 g (also equal to 73.6 mmol) of potassium hydroxide, 30 mL of anhydrous toluene and 3 g (also equal to 9.2 mmol) of the bis(4-bromophenyl)amine are added into a first Schrank flask, and then applying three nitrogen-vacuum cycles to obtain a second mixing solution; 82.9 mg (also equal to 0.46 mmol) 1,10-phenanthroline and 87.61 mg (also equal to 0.46 mmol) cuprous iodide are added into the second mixing solution, and then applying another three nitrogen-vacuum cycles to obtain a third mixing solution, and the third mixing solution is heated to 110° C. to perform a Ullmann reaction for 24 h to obtain a first reacted product; dichloromethane and water are used to extract the first reacted product for three times after the Ullmann reaction, each time of the extraction uses 10 mL of the dichloromethane and 20 mL of the water to combine organic phases to obtain a first extracted product; the first extracted product is dried with anhydrous sodium sulfate to obtain a first dried product; the first dried product is purified by column chromatography after a rotary evaporation; an eluent of the column chromatography includes the dichloromethane and petroleum ether, and a volume ratio of the dichloromethane: the petroleum ether is 3:1, and 3.14 g of 4-naphthyl-4',4"-dibromotriphenylamine is obtained, which illustrates a yield of 76%.

(3) 2.25 g (also equal to 4.96 mmol) of the 4-naphthyl-4',4"-dibromotriphenylamine, 3.02 g (also equal to 11.91 mmol) of bis(pinacolato)diboron, 2.43 g (also equal to 24.8 mmol) of potassium acetate and 182.93 mg (also equal to 0.25 mmol) of [1,1'-bis(diphenylphosphino)ferrocene]dichloropalladium(II) are added to a second Schrank flask, and then applying three nitrogen-vacuum cycles to obtain a first mixture; the first mixture is added with 49.6 mL of 1,4-dioxane served as a solvent by using a syringe, and then applying another three nitrogen-vacuum cycles to obtain a fourth mixing solution, and the fourth mixing solution performs a first Suzuki coupling reaction in 110° C. for 12 h to obtain a second reacted product; the dichloromethane (3*10 mL) and the water (20 mL) are used to extract the second reacted product and combine the organic phases after the first Suzuki coupling reaction to obtain a second extracted product, and the second extracted product is dried with the anhydrous sodium sulfate; and then 2.29 g of N-bis(4-pinacol borate phenyl)-1-naphthylamine is obtained after the rotatory evaporation, which illustrates a yield of 85%.

(4) 1.64 g (also equal to 3 mmol) of the N-bis(4-pinacol borate phenyl)-1-naphthylamine, 1.79 g (also equal to 6.9 mmol) of 5-Br-phenanthroline, 173.34 mg (also equal to 0.15 mmol) of tetrakis(triphenylphosphine)palladium and 2.07 g (15 mmol) of potassium carbonate are added into a third Schrank flask, and then applying three nitrogen-vacuum cycles to obtain a second mixture; the second mixture is added with 30 mL of the 1,4-dioxane and 10 mL of the water by using a syringe to obtain a fifth mixing solution, and the fifth mixing solution performs a second Suzuki coupling reaction in 110° C. for 12 h to obtain a second material; the obtained second material is added into deionized water for deionization after the second Suzuki coupling reaction, then the deionized material is dried, and the dried material is washed with methanol to obtain 1.71 g of a target ligand 7, which illustrates a yield of 88%.

Embodiment 8

A structure of the polydentate organic ligand 8 is expressed by a structural formula as follows:

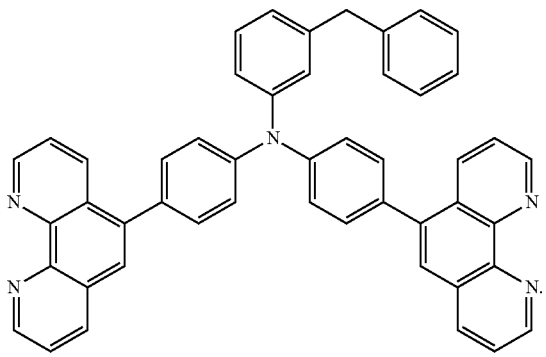 [SMILES: c1ccc(Cc2cccc(N(c3ccc(-c4cc5cccnc5c5ncccc45)cc3)c3ccc(-c4cc5cccnc5c5ncccc45)cc3)c2)cc1]

(1) 5 g (also equal to 29.6 mmol) of diphenylamine is dissolved in 30 mL of N, N-dimethylformamide the first obtained mixture is discharged into the ice-water mixture for precipitation to obtain a N, N-dimethylformamide solution of diphenylamine; 12.12 g (also equal to 68.08 mmol) of NBS is dissolved in 60 mL of the N, N-dimethylformamide to obtain a N, N-dimethylformamide solution of NBS, and the N, N-dimethylformamide solution of NBS is dropped to the N, N-dimethylformamide solution of diphenylamine to obtain a first mixing solution; the first mixing solution is stirred at room temperature for 24 h to perform a bromination reaction; the first obtained material is discharged into the ice-water mixture for precipitation after the bromination reaction; and then the precipitate is filtered and dried under vacuum to obtain 8.65 g of bis(4-bromophenyl)amine, which illustrates a yield of 89%.

(2) 2.96 g (also equal to 11.96 mmol) of benzyl bromide, 4.13 g (also equal to 73.6 mmol) of potassium hydroxide, 30 mL of anhydrous toluene and 3 g (also equal to 9.2 mmol) of the bis(4-bromophenyl)amine are added into a first Schrank flask, and then applying three nitrogen-vacuum cycles to obtain a second mixing solution; 82.9 mg (also equal to 0.46 mmol) 1,10-phenanthroline and 87.61 mg (also equal to 0.46 mmol) cuprous iodide are added into the second mixing solution, and then applying another three nitrogen-vacuum cycles to obtain a third mixing solution, and the third mixing solution is heated to 110° C. to perform a Ullmann reaction for 24 h to obtain a first reacted product; dichloromethane and water are used to extract the first reacted product for three times after the Ullmann reaction, each time of the extraction uses 10 mL of the dichloromethane and 20 mL of the water to combine organic phases to obtain a first extracted product; the first extracted product is dried with anhydrous sodium sulfate to obtain a first dried product; the first dried product is purified by column chromatography after a rotary evaporation; an eluent of the column chromatography includes the dichloromethane and petroleum ether, and a volume ratio of the dichloromethane: the petroleum ether is 3:1 to obtain 3.56 g of 3-benzyl-4', 4"-dibromotriphenylamine, which illustrates a yield of 79%.

(3) 2.45 g (also equal to 4.96 mmol) of the 3-benzyl-4', 4"-dibromotriphenylamine, 3.02 g (also equal to 11.91 mmol) of bis(pinacolato)diboron, 2.43 g (also equal to 24.8 mmol) of potassium acetate and 182.93 mg (also equal to 0.25 mmol) of [1,1'-bis(diphenylphosphino)ferrocene]dichloropalladium(II) are added to a second Schrank flask, and then applying three nitrogen-vacuum cycles to obtain a first mixture; the first mixture is added with 49.6 mL of 1,4-dioxane served as a solvent by using a syringe, and then applying another three nitrogen-vacuum cycles to obtain a fourth mixing solution, and the fourth mixing solution performs a first Suzuki coupling reaction in 110° C. for 12 h to obtain a second reacted product; the dichloromethane (3*10 mL) and the water (20 mL) are used to extract the second reacted product and combine the organic phases after the first Suzuki coupling reaction to obtain a second extracted product, and the second extracted product is dried with the anhydrous sodium sulfate; and then 2.45 g of 3-phenylmethyltriphenylamine pinacol borate ester is obtained after the rotatory evaporation, which illustrates a yield of 85%.

(4) 1.76 g (also equal to 3 mmol) of the 3-phenylmethyltriphenylamine pinacol borate ester, 1.79 g (also equal to 6.9 mmol) of 5-Br-phenanthroline, 173.34 mg (also equal to 0.15 mmol) of tetrakis(triphenylphosphine)palladium and 2.07 g (15 mmol) of potassium carbonate are added into a third Schrank flask, and then applying three nitrogen-vacuum cycles to obtain a second mixture; the second mixture is added with 30 mL of the 1,4-dioxane and 10 mL of the water by using a syringe to obtain a fifth mixing solution, and the fifth mixing solution performs a second Suzuki coupling reaction in 110° C. for 12 h to obtain a second material; the obtained second material is added into deionized water for deionization after the second Suzuki coupling reaction, then the deionized material is dried, and the dried material is washed with methanol to obtain 1.81 g of a target ligand 8, which illustrates a yield of 87%.

Embodiment 9

A structure of the polydentate organic ligand 9 is expressed by a structural formula as follows:

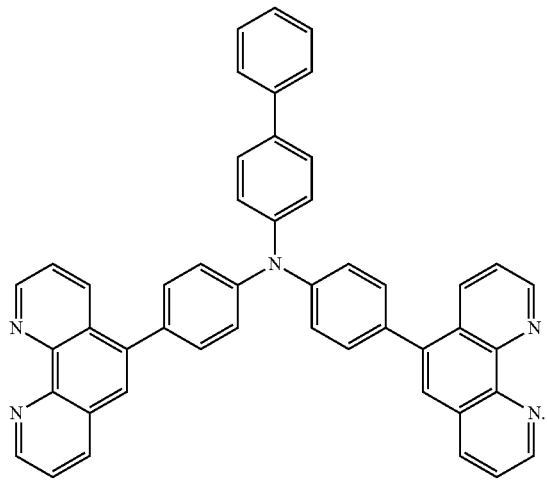 [SMILES: c1ccc(-c2ccc(N(c3ccc(-c4cc5cccnc5c5ncccc45)cc3)c3ccc(-c4cc5cccnc5c5ncccc45)cc3)cc2)cc1]

(1) 5 g (also equal to 29.6 mmol) of diphenylamine is dissolved in 30 mL of N, N-dimethylformamide the first obtained mixture is discharged into the ice-water mixture for precipitation to obtain a N, N-dimethylformamide solution of diphenylamine; 12.12 g (also equal to 68.08 mmol) of NBS is dissolved in 60 mL of the N, N-dimethylformamide to obtain a N, N-dimethylformamide solution of NBS, and the N, N-dimethylformamide solution of NBS is dropped to the N, N-dimethylformamide solution of diphenylamine to obtain a first mixing solution; the first mixing solution is stirred at room temperature for 24 h to perform a bromination reaction; the first obtained material is discharged into the ice-water mixture for precipitation after the bromination reaction; and then the precipitate is filtered and dried under vacuum to obtain 8.65 g of bis(4-bromophenyl)amine, which illustrates a yield of 89%.

(2) 2.79 g (also equal to 11.96 mmol) of 4-bromobiphenyl, 4.13 g (also equal to 73.6 mmol) of potassium hydroxide, 30 mL of anhydrous toluene and 3 g (also equal to 9.2 mmol) of the bis(4-bromophenyl)amine are added into a first Schrank flask, and then applying three nitrogen-vacuum cycles to obtain a second mixing solution; 82.9 mg (also equal to 0.46 mmol) 1,10-phenanthroline and 87.61 mg (also equal to 0.46 mmol) cuprous iodide are added into the second mixing solution, and then applying another three nitrogen-vacuum cycles to obtain a third mixing solution, and the third mixing solution is heated to 110° C. to perform a Ullmann reaction for 24 h to obtain a first reacted product; dichloromethane and water are used to extract the first reacted product for three times after the Ullmann reaction, each time of the extraction uses 10 mL of the dichloromethane and 20 mL of the water to combine organic phases to obtain a first extracted product; the first extracted product is dried with anhydrous sodium sulfate to obtain a first dried product; the first dried product is purified by column chromatography after a rotary evaporation; an eluent of the column chromatography includes the dichloromethane and petroleum ether, and a volume ratio of the dichloromethane: the petroleum ether is 3.5:1, and 3.47 g of 4-phenyl-4',4"-dibromotriphenylamine is obtained, which illustrates a yield of 79%.

(3) 2.38 g (also equal to 4.96 mmol) of the 4-phenyl-4', 4"-dibromotriphenylamine, 3.02 g (also equal to 11.91 mmol) of bis(pinacolato)diboron, 2.43 g (also equal to 24.8 mmol) of potassium acetate and 182.93 mg (also equal to 0.25 mmol) of [1,1'-bis(diphenylphosphino)ferrocene]dichloropalladium(II) are added to a second Schrank flask, and then applying three nitrogen-vacuum cycles to obtain a first mixture; the first mixture is added with 49.6 mL of 1,4-dioxane served as a solvent by using a syringe, and then applying another three nitrogen-vacuum cycles to obtain a fourth mixing solution, and the fourth mixing solution performs a first Suzuki coupling reaction in 110° C. for 12 h to obtain a second reacted product; the dichloromethane (3*10 mL) and the water (20 mL) are used to extract the second reacted product and combine the organic phases after the first Suzuki coupling reaction to obtain a second extracted product, and the second extracted product is dried with the anhydrous sodium sulfate; and then 2.29 g of 4-phenyltriphenylamine pinacol borate ester is obtained after the rotary evaporation, which illustrates a yield of 81%.

(4) 1.72 g (also equal to 3 mmol) of the 4-phenyltriphenylamine pinacol borate ester, 1.79 g (also equal to 6.9 mmol) of 5-Br-phenanthroline, 173.34 mg (also equal to 0.15 mmol) of tetrakis(triphenylphosphine)palladium and 2.07 g (15 mmol) of potassium carbonate are added into a third Schrank flask, and then applying three nitrogen-vacuum cycles to obtain a second mixture; the second mixture is added with 30 mL of the 1,4-dioxane and 10 mL of the water by using a syringe to obtain a fifth mixing solution, and the fifth mixing solution performs a second Suzuki coupling reaction in 110° C. for 12 h to obtain a second material; the obtained second material is added into deionized water for deionization after the second Suzuki coupling reaction, then the deionized material is dried, and the dried material is washed with methanol to obtain 1.78 g of a target ligand 9, which illustrates a yield of 88%.

Embodiment 10

The target ligand 1 is polymerized with $Fe(BF_4)_2 \cdot 6H_2O$ to obtain a metallo-supramolecular polymer marked 1.

1.2 mg of the target ligand 1 prepared in the embodiment 1 is weighed to dissolve in 20 mL of trichloromethane to obtain a ligand solution with a concentration of $10^{-4}$ mole per litter (mol/L). The ligand solution is transferred to a beaker with a diameter of 4.5 cm, and then 67.5 mg of $Fe(BF_4)_2 \cdot 6H_2O$ is dissolved in 20 mL of pure water to obtain a metal ion solution with a concentration of $10^{-2}$ mol/L. The metal ion solution is dropped into a layer of the trichloromethane to obtain a liquid-liquid interface. A metallo-supramolecular polymer film is formed at the liquid-liquid interface after 4 days of standing, and the film is transferred to ITO and rinsed with water and the trichloromethane in turn, and dried to obtain the metallo-supramolecular polymer marked 1.

Embodiment 11

The target ligand 2 is polymerized with $Cu(ClO_4)_2 \cdot 6H_2O$ to obtain a metallo-supramolecular polymer marked 2.

2.53 mg of the target ligand 2 prepared in the embodiment 2 is weighed to dissolve in 20 mL of trichloromethane to obtain a ligand solution with a concentration of $2 \times 10^4$ mol/L. The ligand solution is transferred to a beaker with a diameter of 4.5 cm, and then 148 mg of $Cu(ClO_4)_2 \cdot 6H_2O$ is dissolved in 20 mL of pure water to obtain a metal ion solution with a concentration of $2 \times 10^{-2}$ mol/L. The metal ion solution is dropped into a layer of the trichloromethane to obtain a liquid-liquid interface. A metallo-supramolecular polymer film is formed at the liquid-liquid interface after 3 days of standing, and the film is transferred to ITO and rinsed with water and the trichloromethane in turn, and dried to obtain the metallo-supramolecular polymer marked 2.

Embodiment 12

The target ligand 3 is polymerized with $Co(OAc)_2 \cdot 4H_2O$ to obtain a metallo-supramolecular polymer marked 3.

1.88 mg of the target ligand 3 prepared in the embodiment 3 is weighed to dissolve in 20 mL of trichloromethane to obtain a ligand solution with a concentration of $1.5 \times 10^{-4}$ mol/L. The ligand solution is transferred to a beaker with a diameter of 4.5 cm, and then 74.7 mg of $Co(OAc)_2$ is dissolved in 20 mL of pure water to obtain a metal ion solution with a concentration of $1.5 \times 10^{-2}$ mol/L. The metal ion solution is dropped into a layer of the trichloromethane to obtain a liquid-liquid interface. A metallo-supramolecular polymer film is formed at the liquid-liquid interface after 5 days of standing, and the film is transferred to ITO and rinsed with water and the trichloromethane in turn, and dried to obtain the metallo-supramolecular polymer marked 3.

Embodiment 13

The target ligand 4 is polymerized with $Cd(ClO_4)_2 \cdot 6H_2O$ to obtain a metallo-supramolecular polymer marked 4.

2.51 mg of the target ligand 4 prepared in the embodiment 4 is weighed to dissolve in 20 mL of trichloromethane to obtain a ligand solution with a concentration of $2 \times 10^{-4}$ mol/L. The ligand solution is transferred to a beaker with a diameter of 4.5 cm, and then 168 mg of $Cd(ClO_4)_2 \cdot 6H_2O$ is dissolved in 20 mL of pure water to obtain a metal ion solution with a concentration of $2 \times 10^{-2}$ mol/L. The metal ion solution is dropped into a layer of the trichloromethane to obtain a liquid-liquid interface. A metallo-supramolecular polymer film is formed at the liquid-liquid interface after 4 days of standing, and the film is transferred to ITO and rinsed with water and the trichloromethane in turn, and dried to obtain the metallo-supramolecular polymer marked 4.

Embodiment 14

The target ligand 5 is polymerized with $Fe(BF_4)_2 \cdot 6H_2O$ to obtain a metallo-supramolecular polymer marked 5.

2.46 mg of the target ligand 5 prepared in the embodiment 5 is weighed to dissolve in 20 mL of trichloromethane to obtain a ligand solution with a concentration of $2 \times 10^{-4}$ mol/L. The ligand solution is transferred to a beaker with a diameter of 4.5 cm, and then 135 mg of $Fe(BF_4)_2 \cdot 6H_2O$ is dissolved in 20 mL of pure water to obtain a metal ion solution with a concentration of $2 \times 10^{-2}$ mol/L. The metal ion solution is dropped into a layer of the trichloromethane to obtain a liquid-liquid interface. A metallo-supramolecular polymer film is formed at the liquid-liquid interface after 4 days of standing, and the film is transferred to ITO and rinsed with water and the trichloromethane in turn, and dried to obtain the metallo-supramolecular polymer marked 5.

Embodiment 15

The target ligand 6 is polymerized with $Fe(BF_4)_2 \cdot 6H_2O$ to obtain a metallo-supramolecular polymer marked 6.

2.68 mg of the target ligand 6 prepared in the embodiment 6 is weighed to dissolve in 20 mL of trichloromethane to obtain a ligand solution with a concentration of $2 \times 10^{-4}$ mol/L. The ligand solution is transferred to a beaker with a diameter of 4.5 cm, and then 135 mg of $Fe(BF_4)^2 \cdot 6H_2O$ is dissolved in 20 mL of pure water to obtain a metal ion solution with a concentration of $2 \times 10^{-2}$ mol/L. The metal ion solution is dropped into a layer of the trichloromethane to obtain a liquid-liquid interface. A metallo-supramolecular polymer film is formed at the liquid-liquid interface after 4 days of standing, and the film is transferred to ITO and rinsed with water and the trichloromethane in turn, and dried to obtain the metallo-supramolecular polymer market 6.

Embodiment 16

The target ligand 7 is polymerized with $Fe(BF_4)^2 \cdot 6H_2O$ to obtain a metallo-supramolecular polymer marked 7.

2.61 mg of the target ligand 7 prepared in the embodiment 7 is weighed to dissolve in 20 mL of trichloromethane to obtain a ligand solution with a concentration of $2 \times 10^{-4}$ mol/L. The ligand solution is transferred to a beaker with a diameter of 4.5 cm, and then 135 mg of $Fe(BF_4)^2 \cdot 6H_2O$ is dissolved in 20 mL of pure water to obtain a metal ion solution with a concentration of $2 \times 10^{-2}$ mol/L. The metal ion solution is dropped into a layer of the trichloromethane to obtain a liquid-liquid interface. A metallo-supramolecular polymer film is formed at the liquid-liquid interface after 4 days of standing, and the film is transferred to ITO and rinsed with water and the trichloromethane in turn, and dried to obtain the metallo-supramolecular polymer market 7.

Embodiment 17

The target ligand 8 is polymerized with $Fe(BF_4)^2 \cdot 6H_2O$ to obtain a metallo-supramolecular polymer marked 8.

2.77 mg of the target ligand 8 prepared in the embodiment 8 is weighed to dissolve in 20 mL of trichloromethane to obtain a ligand solution with a concentration of $2 \times 10^{-4}$ mol/L. The ligand solution is transferred to a beaker with a diameter of 4.5 cm, and then 135 mg of $Fe(BF_4)^2 \cdot 6H_2O$ is dissolved in 20 mL of pure water to obtain a metal ion solution with a concentration of $2 \times 10^{-2}$ mol/L. The metal ion solution is dropped into a layer of the trichloromethane to obtain a liquid-liquid interface. A metallo-supramolecular polymer film is formed at the liquid-liquid interface after 4 days of standing, and the film is transferred to ITO and rinsed with water and the trichloromethane in turn, and dried to obtain the metallo-supramolecular polymer marked 8.

Embodiment 18

The target ligand 9 is polymerized with $Fe(BF_4)_2 \cdot 6H_2O$ to obtain a metallo-supramolecular polymer marked 9.

2.71 mg of the target ligand 9 prepared in the embodiment 9 is weighed to dissolve in 20 mL of trichloromethane to obtain a ligand solution with a concentration of $2 \times 10^{-4}$ mol/L. The ligand solution is transferred to a beaker with a diameter of 4.5 cm, and then 135 mg of $Fe(BF_4)_2 \cdot 6H_2O$ is dissolved in 20 mL of pure water to obtain a metal ion solution with a concentration of $2 \times 10^{-2}$ mol/L. The metal ion solution is dropped into a layer of the trichloromethane to obtain a liquid-liquid interface. A metallo-supramolecular polymer film is formed at the liquid-liquid interface after 4 days of standing, and the film is transferred to ITO and rinsed with water and the trichloromethane in turn, and dried to obtain the metallo-supramolecular polymer marked 9.

Characterization and Property Tests

1) FIG. 1 illustrates the hydrogen nuclear magnetic resonance (NMR) spectrum of the triphenylamine pinacol borate ester prepared in the embodiment 1, and an inset in FIG. 1 is a partial enlargement. As shown in FIG. 1, $^1$H NMR (400 million hertz (MHz), $CHCl_3$) δ 7.67 (d, J=8.5 hertz (Hz), 4H), 7.29-7.23 (m, 3H), 7.08 (dd, J=19.2, 8.5 Hz, 7H), 1.33 (s, 25H). A peak position and an integral peak area are consistent with the structure of the triphenylamine pinacol borate ester, indicating a successful synthesis of the triphenylamine pinacol borate ester.

Figure 2:
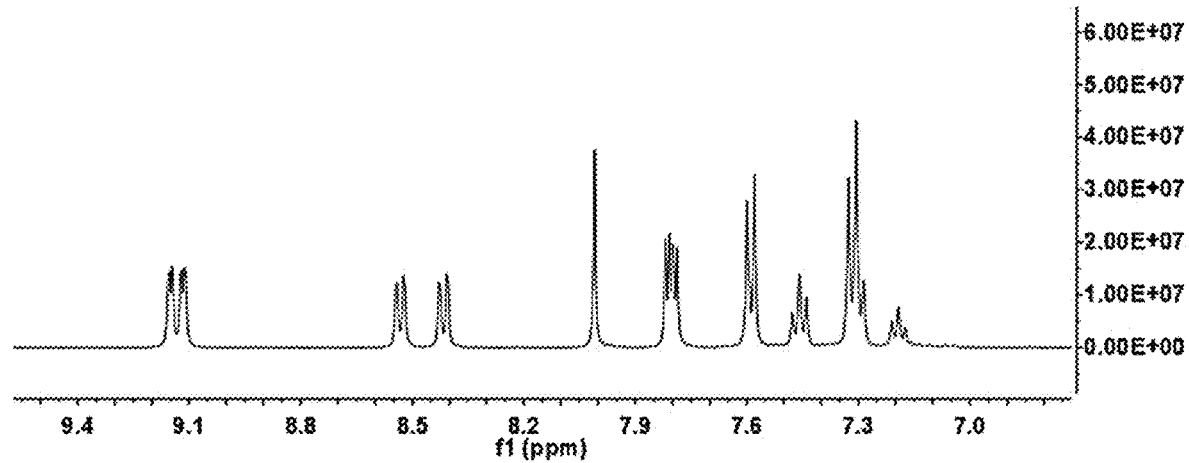
FIG. 2 illustrates a hydrogen NMR spectrum of a target ligand 1 according to the embodiment 1 of the disclosure.

2) FIG. 2 illustrates the hydrogen NMR spectrum of the target ligand 1 prepared in the embodiment 1. As shown in FIG. 2, $^1$H NMR (400 MHz, DMSO) δ 9.13 (ddd, J=14.3, 4.1, 1.4 Hz, 4H), 8.53 (dd, J=8.1, 1.3 Hz, 2H), 8.42 (dd, J=8.3, 1.3 Hz, 2H), 8.01 (s, 2H), 7.80 (dd, J=8.1, 4.2 Hz, 4H), 7.59 (d, J=8.4 Hz, 4H), 7.46 (t, J=7.8 Hz, 2H), 7.31 (t, J=8.0 Hz, 6H), 7.19 (t, J=7.3 Hz, 1H), the peak position and the integral peak area are consistent with the structure of the target ligand 1, indicating the successful preparation of the target ligand 1.

Figure 3:
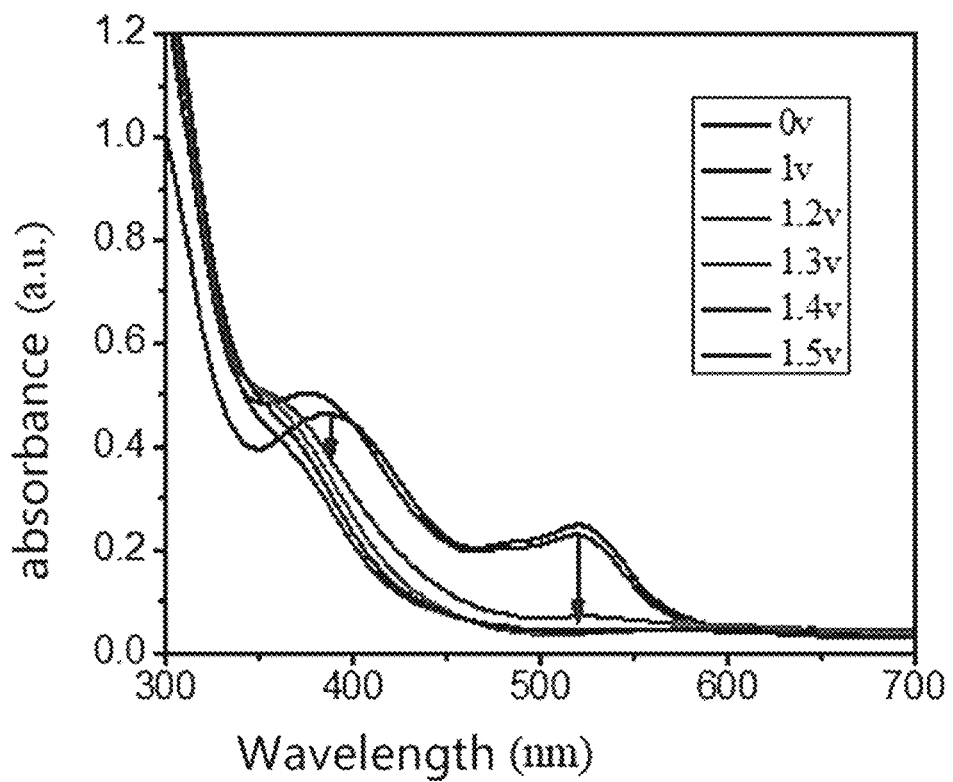
FIG. 3 illustrates an electrochromatogram of a metallo-supramolecular polymer marked 1 according to an embodiment 10 of the disclosure.

3) FIG. 3 illustrates the electrochromatogram of the metallo-supramolecular polymer marked 1 prepared in the embodiment 10, the test method includes: applying different range voltages to a working electrode in Amperometric i-t Curve mode through an electrochemical workstation, while monitoring a change in absorbance at different wavelengths with an ultraviolet-visible-near infrared spectroscopy (UV-Vis-NIR Spectroscopy).

As shown in FIG. 3, when the external voltage is increased from 0 V to 1.2 V, the absorption spectrum changes and the film color changes from red to green, indicating that ferrous ions in the metallo-supramolecular polymer are oxidized to trivalent iron ions when the voltage is increased to 1.2 V, thus changing the absorption spectrum and macroscopically manifesting as a change in the film color.

Figure 4:
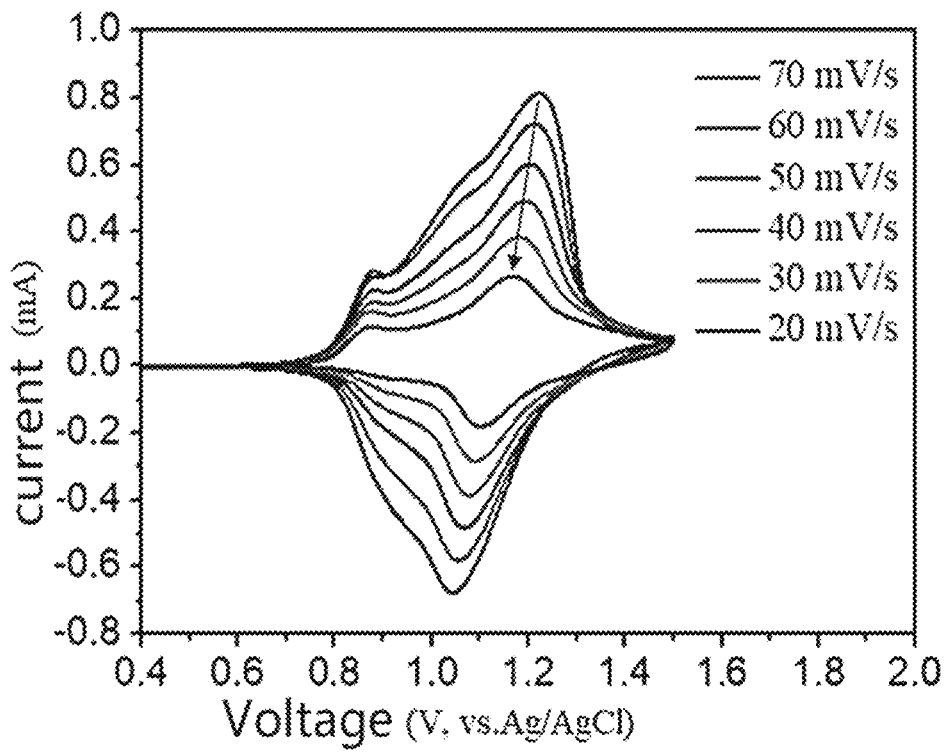
FIG. 4 illustrates a cyclic voltammogram of the metallo-supramolecular polymer marked 1 according to the embodiment 10 of the disclosure.

4) The cyclic voltammetry performance test of the metallo-supramolecular polymer marked 1 prepared in the embodiment 10 is performed as follows: taking the ITO containing the thin film of the metallo-supramolecular polymer in the embodiment 10 as a working electrode, platinum wire as a counter electrode, and Ag/AgCl as a reference electrode to form a three-electrode system, and taking 0.1 mol/L acetonitrile solution of tetra-n-butylammonium perchlorate (TBAP) as an electrolyte. Based on the above three-electrode system, the cyclic voltammogram performance test is performed in the electrochemical workstation with a scan rate range between 20 millivolt per second (mV/s) and 70 mV/s, and the obtained results are shown in FIG. 4. FIG. 4 illustrates the cyclic voltammogram of the metallo-supramolecular polymer marked 1 in the embodiment 10. As shown in FIG. 4, it can be seen that the metallo-supramolecular polymer marked 1 has a pair of reversible redox potentials, and the corresponding redox current increases with an increase of the scan rate of the voltage.

Figure 5:
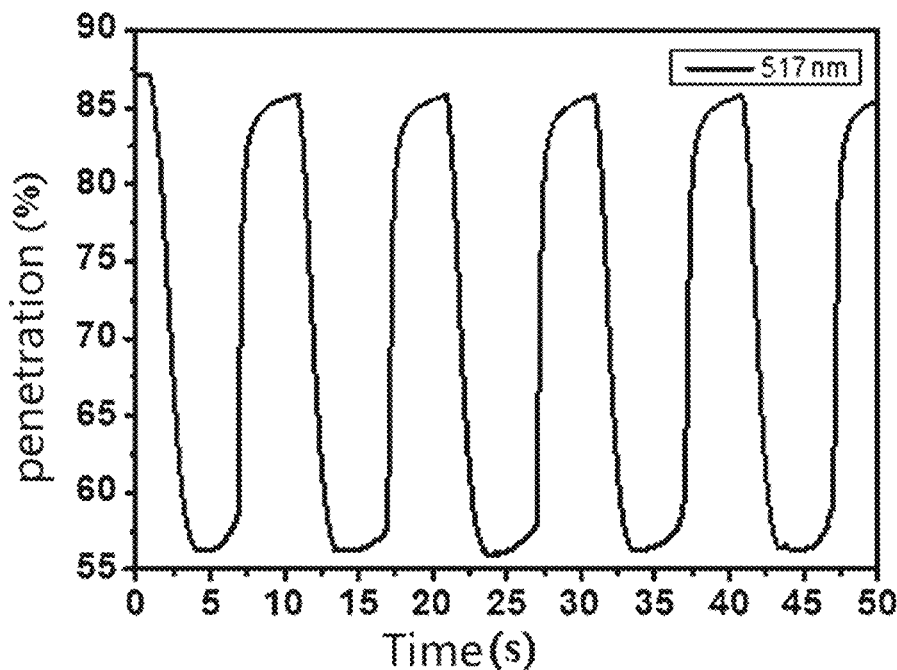
FIG. 5 illustrates an electrochromic response time spectrogram of the metallo-supramolecular polymer marked 1 according to the embodiment 10 of the disclosure.

5) FIG. 5 illustrates the electrochromic response time spectrogram of the metallo-supramolecular polymer marked 1 in the embodiment 10. The test is performed by applying a square wave voltage of 0.00-1.30 voltage (V) to the working electrode in Chronoamperometry mode through an electrochemical workstation, while monitoring change in the absorption spectrum of the metallo-supramolecular polymer 1 at 517 nm with the UV-Vis-NIR Spectroscopy for duration of 10 seconds. As shown in FIG. 5, a coloring time is 1.6 second, and a fading time is 1.5 second, which is better than the values reported in the prior art (YuK, Yang T, YuanF, et al. Self-assembled flexible metallo-supramolecular film based on Fe (II) ion and triphenylamine-substituted alkyl terpyridine towards electrochromic application[J]. Dyes and Pigments, 2021(2):109623.). The fast response speed demonstrates that introducing the structure of the triphenylamine effectively attenuates buildup of the chain in the polymer and accelerates transport speed of electrolyte ions.

Figure 6:
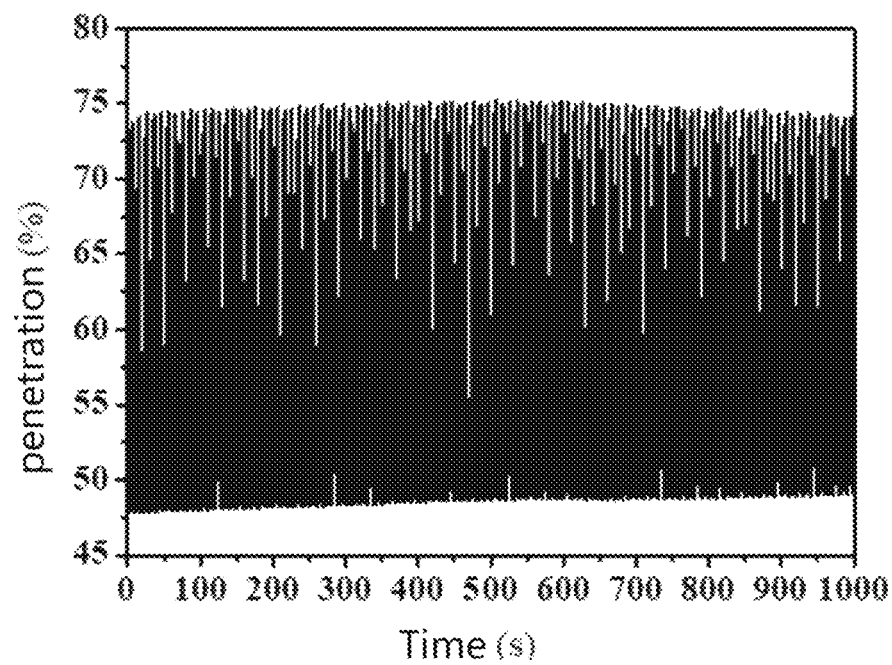
FIG. 6 illustrates an electrochromic stability spectrogram of the metallo-supramolecular polymer marked 1 according to the embodiment 10 of the disclosure.

6) FIG. 6 illustrates the electrochromic stability spectrogram of the metallo-supramolecular polymer marked 1 in the embodiment 10. As can be seen from FIG. 6, after 100 cycles, the curve does not decay significantly, proving that the structure of the metallo-supramolecular polymer marked 1 has stable electrochromic conversion performance.

Figure 7:
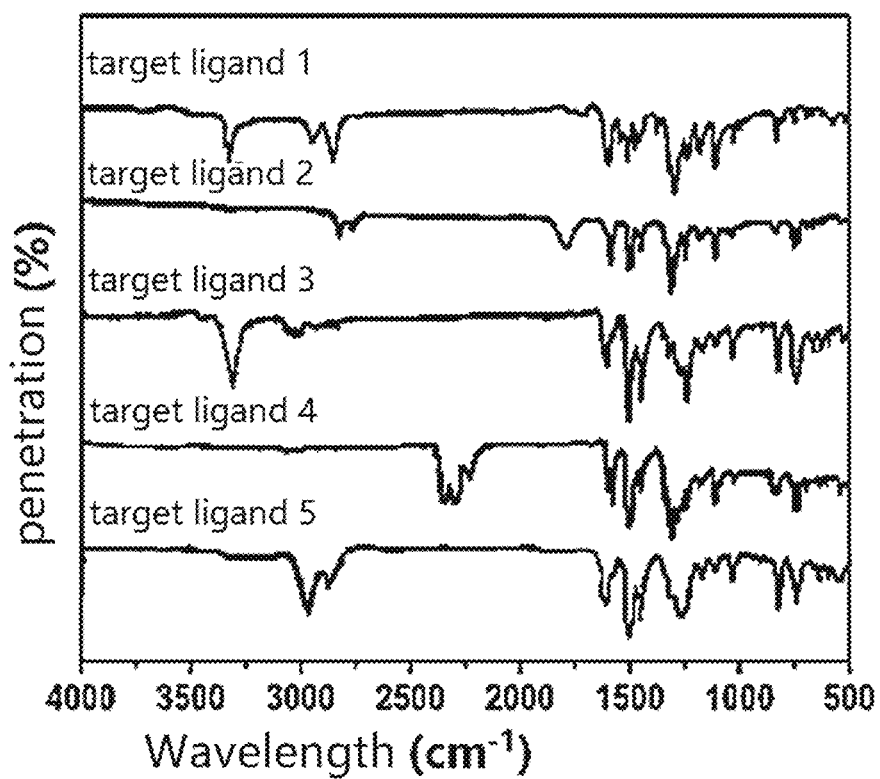
FIG. 7 illustrates infrared spectrograms of target ligands 1-5 prepared by embodiments 1 to 5.
Figure 8:
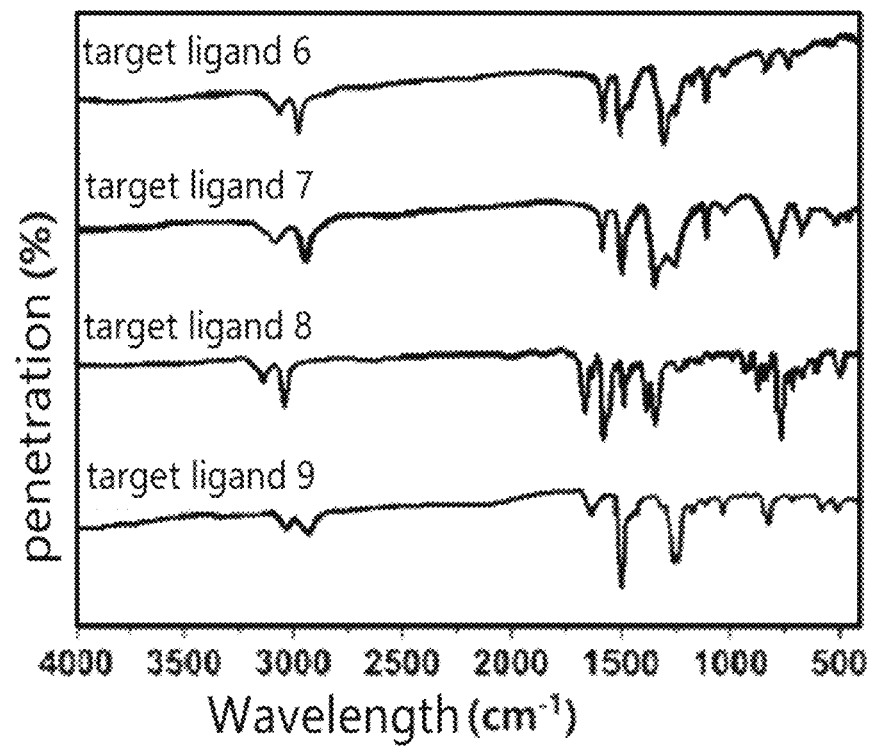
FIG. 8 illustrates infrared spectrograms of target ligands 6-9 prepared by embodiments 6 to 9.

7) FIG. 7 illustrates the infrared spectrograms of the target ligands 1-5 prepared in the embodiments 1-5, and FIG. 8 illustrates the infrared spectrograms of the target ligands 6-9 prepared in the embodiments 6-9. As can be seen from FIGS. 7-8, the target ligands prepared in the embodiments 1-9 have absorption peaks with characteristic functional group structures, such as the absorption peak of a C=N at 1598 $cm^{-1}$; the absorption peak of a $CH_3O$— (also referred to a methoxy group) at 2830-2850 $cm^{-1}$; the absorption peak of an alkynyl group at 3300 $cm^{-1}$; and the absorption peak of a —CN (also referred to a cyano group) at 2220-2230 $cm^{-1}$, indicating the successful preparation of the target ligands.

Solubility tests are performed on the metallo-supramolecular polymers prepared in the embodiment 10-18, and concentrations of the solutions formed by the different metallo-supramolecular polymers in different solvents are 2 mg/mL; and results obtained are shown in Table 1.

TABLE 1

Solubility of the metallo-supramolecular polymers prepared in the embodiments 10-18 in six common solvents

| Metallo-supra-molecular polymer | Solvent | | | | | |
| --- | --- | --- | --- | --- | --- | --- |
| | NMP | DMF | DMSO | $CH_3OH$ | THF | $CHCL_3$ |
| Embodiment 10 | ++ | ++ | + | ++ | +− | ++ |
| Embodiment 11 | ++ | ++ | + | ++ | −− | ++ |
| Embodiment 12 | ++ | ++ | + | ++ | −− | ++ |
| Embodiment 13 | ++ | ++ | + | ++ | −− | ++ |
| Embodiment 14 | ++ | ++ | + | ++ | −− | ++ |
| Embodiment 15 | ++ | ++ | + | ++ | −− | ++ |
| Embodiment 16 | ++ | ++ | + | ++ | −− | ++ |
| Embodiment 17 | ++ | ++ | + | ++ | −− | ++ |
| Embodiment 18 | ++ | ++ | + | ++ | −− | ++ |

Note:
++ illustrates soluble at room temperature;
+ illustrates soluble when heated;
+− illustrates partially soluble;
− illustrates insoluble when heated.

The above descriptions are only illustrated embodiments of the disclosure, and it should be noted that for those skilled in the related art, improvements and embellishments can be made without departing from the principles of the disclosure. These improvements and embellishments should also be considered as the scope of the protection of the disclosure.

What is claimed is:

1. A preparation method of a metallo-supramolecular polymer, comprising:

mixing diphenylamine, N-bromosuccinimide and a first organic solvent to perform a bromination reaction, thereby to obtain bis(4-bromophenyl)amine;

mixing the bis(4-bromophenyl)amine, an X-R compound, a first alkali, a first catalyst and a second organic solvent to perform a Ullmann reaction, thereby to obtain a dibromo compound;

mixing the dibromo compound, bis(pinacolato)diboron, a second alkali, a second catalyst and a third organic solvent to perform a first Suzuki coupling reaction, thereby to obtain a triphenylamine pinacol borate ester compound;

mixing the triphenylamine pinacol borate ester compound, 5-Br-phenanthroline, a third alkali, a third catalyst and a fourth organic solvent to perform a second Suzuki coupling reaction, thereby to obtain a polydentate organic ligand having a structure of triphenylamine-phenanthroline; and mixing a solution of the polydentate organic ligand and an aqueous solution of metal salt to polymerize, thereby to obtain the metallo-supramolecular polymer;

wherein the structure of triphenylamine-phenanthroline is expressed by Formula I:

(Formula I)

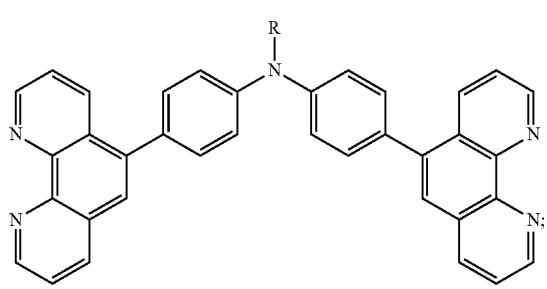

wherein in the Formula I, R is a group represented by the following structure:

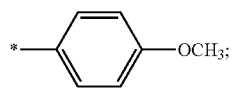

wherein in the X-R compound, X is a halogen, and R is the group represented by the following structure:

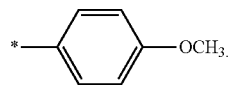 [SMILES: *c1ccc(OC)cc1]

2. The preparation method according to claim 1, wherein the metal salt comprises one of $Fe(BF_4)_2 \cdot 6H_2O$, $Cu(ClO_4)_2 \cdot 6H_2O$, $Co(OAc)_2 \cdot 4H_2O$ and $Cd(ClO_4)_2 \cdot 6H_2O$; a concentration of the solution of the polydentate organic ligand is between $1 \times 10^{-4}$ mole per liter (mol/L) and $2 \times 10^{-4}$ mol/L, a concentration of the aqueous solution of the metal salt is between $1 \times 10^{-2}$ mol/L and $2 \times 10^{-2}$ mol/L, and a volume ratio of the solution of the polydentate organic ligand:the aqueous solution of the metal salt is 1:1.

3. The preparation method according to claim 1, wherein a molar ratio of the diphenylamine:the N-bromosuccinimide is 1:(2-2.5); a temperature of the bromination reaction is room temperature, and a time of the bromination reaction is between 24 hours (h) and 36 h.

4. The preparation method according to claim 1, wherein the first alkali comprises one selected from the group consisting of potassium hydroxide, sodium hydroxide, potassium carbonate, sodium carbonate and cesium carbonate; the first catalyst comprises phenanthroline and cuprous iodide; a molar ratio of the bis(4-bromophenyl)amine:the X-R compound:the first alkali is 1:(1-1.5):(8-9); a molar ratio of the cuprous iodide:the phenanthroline is (0.03-0.05):(0.03-0.05); a molar ratio of the bis(4-bromophenyl)amine: the cuprous iodide is 1:(0.03-0.05); and a temperature of the Ullmann reaction is between 110 degrees Celsius (° C.) and 120° C., and a time of the Ullmann reaction is between 20 h and 30 h.

5. The preparation method according to claim 1, wherein the second alkali comprises one selected from the group consisting of potassium acetate, sodium carbonate, lithium carbonate and potassium phosphate; the second catalyst comprises [1,1'-bis(diphenylphosphino)ferrocene]dichloropalladium(II); a molar ratio of the dibromo compound:the bis(pinacolato)diboron:the second alkali:the second catalyst is 1:(2-2.5):(5-8):(0.03-0.05); a temperature of the first Suzuki coupling reaction is between 110° C. and 120° C., and a time of the first Suzuki coupling reaction is 12 h.

6. The preparation method according to claim 1, wherein the third alkali comprises potassium carbonate; the third catalyst comprises tetrakis(triphenylphosphine)palladium; a molar ratio of the triphenylamine pinacol borate ester compound:the 5-Br-phenanthroline:the third catalyst:the third alkali is 1:(2-2.5):(0.03-0.05):(5-8); a temperature of the second Suzuki coupling reaction is between 110° C. and 120° C. and a time of the second Suzuki coupling reaction is 12 h.

* * * * *